US008586787B2

(12) United States Patent
Nakagawa

(10) Patent No.: US 8,586,787 B2
(45) Date of Patent: Nov. 19, 2013

(54) PROCESS FOR PRODUCING (METH)ACRYLIC ACID

(75) Inventor: Satoshi Nakagawa, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 98 days.

(21) Appl. No.: 13/318,639

(22) PCT Filed: May 7, 2010

(86) PCT No.: PCT/JP2010/057811
§ 371 (c)(1),
(2), (4) Date: Nov. 3, 2011

(87) PCT Pub. No.: WO2010/131604
PCT Pub. Date: Nov. 18, 2010

(65) Prior Publication Data
US 2012/0046433 A1   Feb. 23, 2012

(30) Foreign Application Priority Data

May 15, 2009   (JP) ................. 2009-119164

(51) Int. Cl.
*C07C 51/43*   (2006.01)

(52) U.S. Cl.
USPC ........................................ 562/600

(58) Field of Classification Search
USPC ................................ 562/600, 608
See application file for complete search history.

(56) References Cited

U.S. PATENT DOCUMENTS

| | | |
|---|---|---|
| 4,893,999 A | 1/1990 | Chmelir et al. |
| 4,920,202 A | 4/1990 | Irie et al. |
| 5,264,495 A | 11/1993 | Irie et al. |
| 5,275,773 A | 1/1994 | Irie et al. |
| 5,385,983 A | 1/1995 | Graham |
| 5,409,771 A | 4/1995 | Dahmen et al. |
| 5,462,972 A | 10/1995 | Smith et al. |
| 5,546,763 A | 8/1996 | Kikuchi et al. |
| 5,597,873 A | 1/1997 | Chambers et al. |
| 5,610,220 A | 3/1997 | Klimmek et al. |
| 5,633,316 A | 5/1997 | Gartner et al. |
| 5,669,894 A | 9/1997 | Goldman et al. |
| 5,674,633 A | 10/1997 | Saunders et al. |
| 5,756,602 A | 5/1998 | Hui et al. |
| 6,164,455 A | 12/2000 | Kakita et al. |
| 6,207,796 B1 | 3/2001 | Dairoku et al. |
| 6,219,636 B1 | 4/2001 | Ihara |
| 6,241,928 B1 | 6/2001 | Hatsuda et al. |
| 6,291,636 B1 | 9/2001 | Miyake et al. |
| 6,472,478 B1 | 10/2002 | Funk et al. |
| 6,503,979 B1 | 1/2003 | Funk et al. |
| 6,710,141 B1 | 3/2004 | Heide et al. |
| 6,867,269 B2 | 3/2005 | Sakamoto et al. |
| 6,875,511 B2 | 4/2005 | Dairoku et al. |
| 6,906,159 B2 | 6/2005 | Dairoku et al. |
| 6,987,151 B2 | 1/2006 | Gartner et al. |
| 7,091,253 B2 | 8/2006 | Dairoku et al. |
| 7,342,130 B2 | 3/2008 | Shibusawa et al. |
| 7,714,164 B2 | 5/2010 | Nakagawa |
| 7,732,635 B2 | 6/2010 | Matsumoto |
| 2004/0110897 A1 | 6/2004 | Sakamoto et al. |
| 2004/0186229 A1 | 9/2004 | Heide et al. |
| 2005/0215734 A1 | 9/2005 | Dairoku et al. |
| 2005/0221457 A1 | 10/2005 | Tsobanakis et al. |
| 2007/0129572 A1 | 6/2007 | Shibusawa et al. |
| 2007/0238898 A1 | 10/2007 | Matsumoto |
| 2008/0004408 A1 | 1/2008 | Stueven et al. |
| 2008/0071111 A1 | 3/2008 | Nakagawa |
| 2009/0188270 A1 | 7/2009 | Takahashi et al. |
| 2009/0298144 A1 | 12/2009 | Tsobanakis et al. |
| 2010/0069583 A1 | 3/2010 | Kasuga et al. |

FOREIGN PATENT DOCUMENTS

| | | |
|---|---|---|
| CA | 2319786 | 2/1999 |
| CN | 1104927 | 7/1995 |
| CN | 1134942 | 11/1996 |
| CN | 1314422 | 9/2001 |
| EP | 0 349 240 | 1/1990 |
| EP | 0 450 923 | 10/1991 |
| EP | 0 450 924 | 10/1991 |
| EP | 0 605 150 | 7/1994 |
| EP | 0 668 080 | 8/1995 |
| EP | 0 812 873 | 12/1997 |
| JP | 6-159831 | 6/1994 |

(Continued)

OTHER PUBLICATIONS

International Search Report issued Jun. 1, 2010 in International (PCT) Application No. PCT/JP2010/057811, of which the present application is the National Stage.

(Continued)

*Primary Examiner* — Brian J Davis
(74) *Attorney, Agent, or Firm* — Wenderoth, Lind & Ponack, L.L.P.

(57) ABSTRACT

A process for producing (meth)acrylic acid, comprising a crystallizing step of supplying a cooling medium from a refrigerator to a crystallizer and returning the cooling medium from the crystallizer to the refrigerator, thereby obtaining a (meth)acrylic acid crystal from a (meth)acrylic acid-containing solution; and a melting step of supplying a heating medium from a refrigerator to the crystallizer and returning the heating medium from the crystallizer to the refrigerator, thereby melting the (meth)acrylic acid crystal; wherein the crystallizing step and the melting step are respectively performed at least once, thereby producing purified (meth)acrylic acid from a crude (meth)acrylic acid solution; temperature of the cooling medium discharged from the refrigerator is maintained constant at temperature T1; temperature of the cooling medium to be returned to the refrigerator is maintained constant at temperature T2; the temperature T2 is adjusted depending on a production amount of the purified (meth)acrylic acid per unit time.

20 Claims, 7 Drawing Sheets

(56) References Cited

FOREIGN PATENT DOCUMENTS

| | | |
|---|---|---|
| JP | 7-224304 | 8/1995 |
| JP | 7-242709 | 9/1995 |
| JP | 8-259606 | 10/1996 |
| JP | 2005-521718 | 7/2005 |
| JP | 2005-207660 | 8/2005 |
| JP | 2007-182437 | 7/2007 |
| JP | 2007-277182 | 10/2007 |
| JP | 2008-74759 | 4/2008 |
| JP | 2008-115103 | 5/2008 |
| WO | 99/42494 | 8/1999 |
| WO | 99/42496 | 8/1999 |
| WO | 99/43720 | 9/1999 |
| WO | 01/16346 | 3/2001 |
| WO | 01/38402 | 5/2001 |
| WO | 2005/016393 | 2/2005 |
| WO | 2005/095320 | 10/2005 |
| WO | 2006/034806 | 4/2006 |
| WO | 2006/087083 | 8/2006 |
| WO | 2006/087084 | 8/2006 |
| WO | 2007/106100 | 9/2007 |
| WO | 2008/027742 | 3/2008 |
| WO | 2008/114745 | 9/2008 |

OTHER PUBLICATIONS

Office Action issued Jun. 27, 2013 in corresponding Chinese Application No. 201080018295.5, with English translation thereof.
Office Action issued Jul. 26, 2013 in Chinese Application No. 201080018465.X, with English translation thereof.

ically produces (meth)acrylic acid comprising a crystallizing step and a melting step.

TECHNICAL FIELD

The present invention relates to a process for producing (meth)acrylic acid comprising a crystallizing step and a melting step.

BACKGROUND ART

Conventionally, a process for industrially producing (meth)acrylic acid by gas-phase catalytic oxidation of a (meth)acrylic acid production raw material has been known. A (meth)acrylic acid-containing gas produced by gas-phase catalytic oxidation of the (meth)acrylic acid production raw material is, for example, collected by a liquid medium to be recovered as a crude (meth)acrylic acid solution, and then, the crude (meth)acrylic acid solution is purified by methods such as distillation, diffusion, extraction, crystallization, or the like.

Patent Literature 1 discloses a method for purifying a crude (meth)acrylic acid solution by crystallization. In the case where a crude (meth)acrylic acid solution is purified by crystallization, cooling is needed for crystallizing (meth)acrylic acid from a crude (meth)acrylic acid solution, and heating is needed for obtaining purified (meth)acrylic acid by melting crystallized (meth)acrylic acid. However, Patent Literature 1 does not specifically describe a method for cooling and heating in the crystallization.

Patent Literature 2 discloses that cooling water generated by an absorption refrigerator is used in a crystallizing step when a crude (meth)acrylic acid solution is purified by crystallization. However, Patent Literature 2 does not describe techniques for stable operation of the refrigerator in the crystallization.

CITATION LIST

Patent Literature

Patent Literature 1
Japanese Unexamined Laid-open Patent Application Publication No. 2008-74759
Patent Literature 2
Japanese Unexamined Laid-open Patent Application Publication No. 2007-277182

SUMMARY OF INVENTION

Technical Problem

When a crude (meth)acrylic acid solution is cooled by a cooling medium to obtain a (meth)acrylic acid crystal, temperature of the cooling medium discharged from a crystallizer tends to be high at the beginning and fall as the progress of crystallizing. Similarly, when the (meth)acrylic acid crystal is heated by a heating medium to be melted, thereby obtaining purified (meth)acrylic acid, temperature of the heating medium discharged from a crystallizer tends to be low at the beginning and rise as the progress of melting. Therefore, in the case where the temperature of the cooling medium or the heating medium discharged from the crystallizer is adjusted by a refrigerator so that the cooling medium or the heating medium is supplied to the crystallizer again, cooling or heating load of the refrigerator changes due to the temperature change of the cooling medium or the heating medium returned to the refrigerator. As a result, operation of the refrigerator is likely to be destabilized.

The above explanation concerns a load change of the refrigerator in a single crystallizing step or a single melting step; however, when the crystallizing step and the melting step are performed repeatedly, a load change of the refrigerator possibly occur between a plurality of the crystallizing step or a plurality of the melting step. For example, in the case where a crude (meth)acrylic acid solution is crystallized and melted to obtain purified (meth)acrylic acid, cooling or heating load of the refrigerator changes depending on production efficiency of the purified (meth)acrylic acid (i.e. a production amount of the purified (meth)acrylic acid per unit time). Also in this case, cooling or heating load of the refrigerator returned to the refrigerator changes, and as a result, operation of the refrigerator is likely to be destabilized.

The present invention has been achieved in view of the above circumstances, and the object of the present invention is to provide a process for producing (meth)acrylic acid that enables operating a refrigerator stably, irrespective of a load change in a crystallizing step and/or a melting step and a production efficiency of purified (meth)acrylic acid.

Solution to Problem

In the case where a load in a crystallizing step or a melting step varies or a production amount of the purified (meth)acrylic acid per unit time is changed, it is thought a method of changing an operation condition of a refrigerator in accordance with that. However, it is difficult to change the operation condition of the refrigerator timely in accordance with a load change of a crystallizer in a single crystallizing step or a single melting step, since that causes the operation of the refrigerator to become complex. And so, in the present invention, it has been found that providing a buffer tank and reducing the temperature change of the cooling medium or the heating medium returned to the refrigerator by the buffer tank is effective in regard to the load change of the crystallizer in a single crystallizing step or a single melting step.

In regard to the load change of the crystallizer between a plurality of the crystallizing step or a plurality of the melting step or the change of the production amount of the purified (meth)acrylic acid per unit time, it has been found that adjusting temperature of the cooling medium or the heating medium returned to the refrigerator realizes stable operation of the refrigerator for a long period.

Thus, a process for producing (meth)acrylic acid of the present invention which solves the above problems comprises: a crystallizing step of supplying a cooling medium from a refrigerator to a crystallizer and returning the cooling medium from the crystallizer to the refrigerator, thereby obtaining a (meth)acrylic acid crystal from a (meth)acrylic acid-containing solution; and a melting step of supplying a heating medium from a refrigerator to the crystallizer and returning the heating medium from the crystallizer to the refrigerator, thereby melting the (meth)acrylic acid crystal; wherein the crystallizing step and the melting step are respectively performed at least once, thereby producing purified (meth)acrylic acid from a crude (meth)acrylic acid solution; temperature of the cooling medium discharged from the refrigerator is maintained constant at temperature T1; temperature of the cooling medium to be returned to the refrigerator is maintained constant at temperature T2 in the crystallizing step by a first adjustment operation and/or a second adjustment operation; the temperature T2 is adjusted depending on a production amount of the purified (meth)acrylic acid per unit time; the first adjustment operation is performed by feeding at least a part of the cooling medium to be returned to the refrigerator from the crystallizer into an upper part of a first buffer tank and discharging the cooling medium from a lower part of the first buffer tank to return to the refrigerator; and the second adjustment operation is performed by feeding at least a part of the cooling medium to be supplied to the crystallizer from the refrigerator and/or the cooling medium to be returned to the refrigerator from the crystallizer into the lower part of the first buffer tank and discharging the cooling medium from the upper part of the first buffer tank to return to the refrigerator.

According to the above producing process, the refrigerator can be stably operated by the first adjustment operation and/or the second adjustment operation, irrespective of a load change in the crystallizing step and a production efficiency of purified (meth)acrylic acid.

An another process for producing (meth)acrylic acid of the present invention comprises: a crystallizing step of supplying a cooling medium from a refrigerator to a crystallizer and returning the cooling medium from the crystallizer to the refrigerator, thereby obtaining a (meth)acrylic acid crystal from a (meth)acrylic acid-containing solution; and a melting step of supplying a heating medium from a refrigerator to the crystallizer and returning the heating medium from the crystallizer to the refrigerator, thereby melting the (meth)acrylic acid crystal; wherein the crystallizing step and the melting step are respectively performed at least once, thereby producing purified (meth)acrylic acid from a crude (meth)acrylic acid solution; temperature of the heating medium discharged from the refrigerator is maintained constant at temperature T3; temperature of the heating medium to be returned to the refrigerator is maintained constant at temperature T4 in the melting step by a third adjustment operation and/or a fourth adjustment operation; the temperature T4 is adjusted depending on a production amount of the purified (meth)acrylic acid per unit time; the third adjustment operation is performed by feeding at least a part of the heating medium to be returned to the refrigerator from the crystallizer into an lower part of a second buffer tank and discharging the heating medium from an upper part of the second buffer tank to return to the refrigerator; and the fourth adjustment operation is performed by feeding at least a part of the heating medium to be supplied to the crystallizer from the refrigerator and/or the heating medium to be returned to the refrigerator from the crystallizer into the upper part of the second buffer tank and discharging the heating medium from the lower part of the second buffer tank to return to the refrigerator.

According to the above producing process, the refrigerator can be stably operated by the third adjustment operation and/or the fourth adjustment operation, irrespective of a load change in the melting step and a production efficiency of purified (meth)acrylic acid.

A still another process for producing (meth)acrylic acid of the present invention comprises: a crystallizing step of supplying a cooling medium from a refrigerator to a crystallizer and returning the cooling medium from the crystallizer to the refrigerator, thereby obtaining a (meth)acrylic acid crystal from a (meth)acrylic acid-containing solution; and a melting step of supplying a heating medium from a refrigerator to the crystallizer and returning the heating medium from the crystallizer to the refrigerator, thereby melting the (meth)acrylic acid crystal; wherein the crystallizing step and the melting step are respectively performed at least once, thereby producing purified (meth)acrylic acid from a crude (meth)acrylic acid solution; temperature of the cooling medium discharged from the refrigerator is maintained constant at temperature T1; temperature of the cooling medium to be returned to the refrigerator is maintained constant at temperature T2 in the crystallizing step by the said first adjustment operation and/or the said second adjustment operation; temperature of the heating medium discharged from the refrigerator is maintained constant at temperature T3; temperature of the heating medium to be returned to the refrigerator is maintained constant at temperature T4 in the melting step by the said third adjustment operation and/or the said fourth adjustment operation; and the temperatures T2 and T4 are adjusted depending on a production amount of the purified (meth)acrylic acid per unit time. According to the above producing process, the refrigerator can be stably operated irrespective of load changes in the crystallizing step and the melting step and a production efficiency of purified (meth)acrylic acid.

The temperatures T1 and T3 are preferably fixed irrespective of the production amount of the purified (meth)acrylic acid per unit time. Thereby, quality and yield of the obtained purified (meth)acrylic acid is easily stabilized.

In the process for producing (meth)acrylic acid, it is preferred that a production amount of the purified (meth)acrylic acid obtained by conducting the crystallizing step and the melting step at least once, respectively, is kept constant and the temperatures T2 and T4 are adjusted depending on a period for producing the purified (meth)acrylic acid. Thereby, quality of the obtained purified (meth)acrylic acid is easily stabilized.

The producing process of the present invention may further comprise the steps of: dehydrating glycerin or 2-methylglycerin to convert to (meth)acrolein; and oxidizing the (meth)acrolein to convert to (meth)acrylic acid, thereby obtaining the crude (meth)acrylic acid solution. Or, the producing process of the present invention may further comprise the step of dehydrating hydroxypropionic acid or 2-methyl-3-hydroxypropionic acid to convert to (meth)acrylic acid, thereby obtaining the crude (meth)acrylic acid solution. The crude (meth)acrylic acid solution used in the producing process of the present invention may be obtained by such processes.

The present invention also provides a process for producing a hydrophilic resin or an absorbent resin, comprising the step of polymerizing a monomeric component(s) including the (meth)acrylic acid obtained by the producing process of the present invention. When (meth)acrylic acid obtained by the producing process of the present invention is used as a monomer for producing a hydrophilic resin such as an absorbent resin and a water-soluble resin, the polymerization reaction is easily controlled and quality of the hydrophilic resin is stabilized, thereby improving various properties such as absorption performance and dispersibility of inorganic substances.

Advantageous Effects of Invention

According to the process for producing (meth)acrylic acid of the present invention, a refrigerator can be stably operated irrespective of a load change in the crystallizing step and/or the melting step and a production efficiency of purified (meth) acrylic acid

DESCRIPTION OF THE PREFERRED EMBODIMENTS

Figure 1:
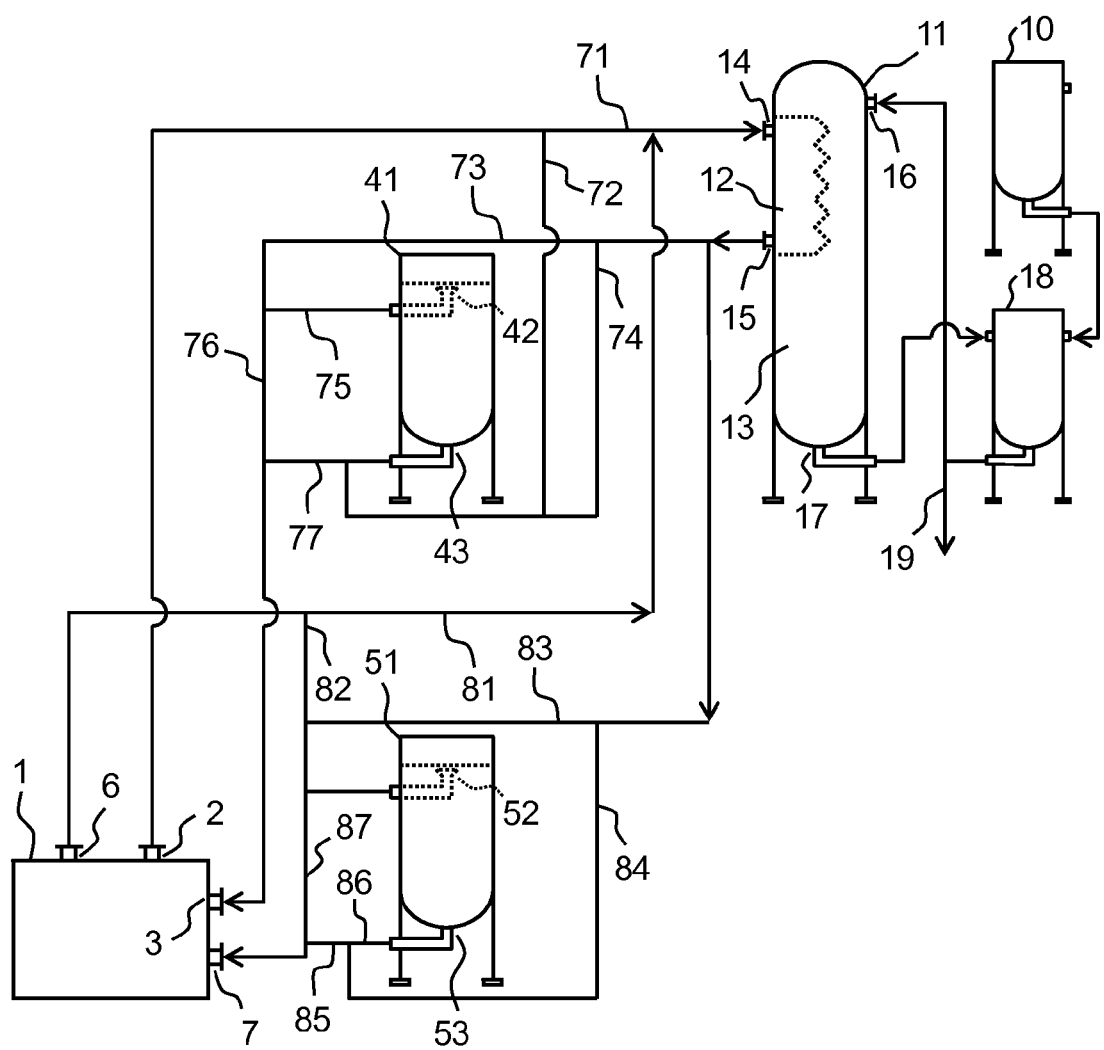
FIG. 1 shows a refrigerator, a crystallizer, a first buffer tank, a second buffer tank and flow paths connecting them.

A process for producing (meth)acrylic acid of the present invention is a process where a crystallizing step and a melting step are respectively performed at least once, thereby producing purified (meth)acrylic acid from a crude (meth)acrylic acid solution.

No particular limitation is placed on the crude (meth) acrylic acid solution, and the crude (meth)acrylic acid solution can be any solution containing (meth)acrylic acid and an impurity thereof. Examples of the impurity include unreacted (meth)acrylic acid production raw materials, water, acetic acid, propionic acid, maleic acid, acetone, acrolein, furfural, formaldehyde, a condensation liquid medium and the like. The crude (meth)acrylic acid solution preferably has (meth) acrylic acid concentration of 80 mass % or more.

In the crystallizing step, a cooling medium is supplied to a crystallizer from a refrigerator and returned to the refrigerator from the crystallizer, thereby obtaining a (meth)acrylic acid crystal from a (meth)acrylic acid-containing solution.

In the melting step, a heating medium is supplied to the crystallizer from a refrigerator and returned to the crystallizer from the crystallizer, whereby the (meth)acrylic acid crystal is melted. In the melting step, the (meth)acrylic acid crystal obtained by the crystallizing step is melted, thereby obtaining a (meth)acrylic acid melt. The obtained (meth)acrylic acid melt may be subjected to the crystallizing step again, or may be treated as the purified (meth)acrylic acid. In the melting step, the (meth)acrylic acid crystal is heated by the heating medium, thereby obtaining the (meth)acrylic acid melt.

In some cases, a sweating operation, by which the (meth) acrylic acid crystal is partially melted and impurities present between the crystals or on the surface of the crystal are washed away, may be performed for the purpose of enhancing the purity of the (meth)acrylic acid melt when the (meth) acrylic acid crystal is melted by heating; and in the present invention, the sweating operation is included in the melting step.

In the present invention, it is only necessary that the crystallizing step and the melting step are respectively performed at least once, and preferably, the crystallizing step and the melting step are performed twice or more times for enhancing the purity of the purified (meth)acrylic acid to be obtained.

The refrigerator used in the producing process of the present invention is not particularly limited as long as it is capable of both cooling the cooling medium and heating the heating medium; and an absorption refrigerator (e.g. an ammonia absorption refrigerator, a water-lithium bromide refrigerator, and the like), a compression refrigerator, an adsorption refrigerator and the like can be used.

The cooling medium and the heating medium are not particularly limited, as long as they are kept in liquid states in the refrigerator and the crystallizer during producing (meth) acrylic acid. The cooling medium may be the same as or different from the heating medium. In the case where the cooling medium and the heating medium are the same, ethylene glycol aqueous solution, glycerin aqueous solution, methanol aqueous solution, or the like is used as the cooling medium and the heating medium.

In the crystallizing step, the cooling medium is supplied to the crystallizer from the refrigerator, thereby crystallizing (meth)acrylic acid from the (meth)acrylic acid-containing solution and discharged from the crystallizer to be returned to the refrigerator. The cooling medium which has been returned to the refrigerator is preferably cooled by the refrigerator and again supplied to the crystallizer.

Temperature of the cooling medium discharged from the refrigerator is not particularly limited as long as it is lower than the melting point of the (meth)acrylic acid-containing solution. The temperature of the cooling medium discharged from the refrigerator is preferably 0° C. or lower, and more preferably −5° C. or lower. As described above, the upper limit of the temperature of the cooling medium discharged from the refrigerator is needed to be lower than the melting point of the (meth)acrylic acid-containing solution; however, the temperature of the cooling medium discharged from the refrigerator is preferably 0° C. or lower so that the amount of the cooling medium required for crystallizing is not too much increased and the size of the crystallizer, pipes for the cooling medium or the like is not too much increased. Meanwhile, the lower limit of the temperature of the cooling medium discharged from the refrigerator is not particularly limited.

The above description concerns the case where the one cooling medium discharged from the refrigerator is used; however, two or more cooling mediums, which have different temperatures from each other, may be used as the cooling medium discharged from the refrigerator. For example, in the case where the cooling medium supplied from the refrigerator includes a first cooling medium and a second cooling medium having lower temperature than the first cooling medium, the first cooling medium preferably has temperature of 0° C. or lower, and the second cooling medium preferably has temperature of −10° C. or lower. In this case, the crystallizing step is preferably performed such that the first cooling medium is supplied to the crystallizer and then the second cooling medium having lower temperature than the first cooling medium is supplied to the crystallizer. When the first cooling medium and the second cooling medium are used in this manner, the purity of the (meth)acrylic acid crystal is easily enhanced and the energy consumption of the refrigerator can be further reduced.

In the melting step, the heating medium is supplied to the crystallizer from the refrigerator, thereby melting the (meth) acrylic acid crystal and discharged from the crystallizer to be returned to the refrigerator. The heating medium which has been returned to the refrigerator is preferably heated by the refrigerator and again supplied to the crystallizer.

Temperature of the heating medium discharged from the refrigerator is not particularly limited as long as it exceeds the melting point of the (meth)acrylic acid crystal. The temperature of the heating medium discharged from the refrigerator is preferably 20° C. or higher, more preferably 25° C. or higher, and preferably 45° C. or lower, more preferably 40° C. or lower. As described above, the lower limit of the temperature of the heating medium discharged from the refrigerator is needed to be higher than the melting point of the (meth) acrylic acid crystal; however, the temperature of the heating medium discharged from the refrigerator is preferably 20° C. or higher so that the amount of the heating medium required for melting is not too much increased and the size of the crystallizer, pipes for the heating medium or the like is not too much increased. Meanwhile, in the case where the temperature of the heating medium discharged from the refrigerator is higher than 45° C., continuous operation of the crystallizer may become difficult or the purity or yield of the obtained (meth)acrylic acid may decline, due to occurrence of polymerization of (meth)acrylic acid in the crystallizer. In addition, it is likely that a refrigerator with high-power specifications is needed or the energy consumption of the refrigerator is increased due to increase in the heating load of the refrigerator. Therefore, the temperature of the heating medium discharged from the refrigerator is preferably 45° C. or lower. In addition, two or more heating mediums, which have different temperatures from each other, may be used as the heating medium discharged from the refrigerator.

In the producing process of the present invention, the temperature of the cooling medium discharged from the refrigerator is maintained constant at temperature T1, and the temperature of the heating medium discharged from the refrigerator is maintained constant at temperature T3. When the temperature of the cooling medium or the heating medium discharged from the refrigerator is maintained constant, crystallizing or melting operation is easily conducted stably in the crystallizer. Further, in cooperation with the temperature of the cooling medium or the heating medium returned to the refrigerator being maintained constant as described below, cooling or heating load of the refrigerator is easily maintained constant, and as a result, the refrigerator can stably work and the consumption energy thereof can be reduced.

Flow rate of the cooling medium or the heating medium discharged from the refrigerator is set appropriately depending on the temperature of the cooling medium or the heating medium discharged from the refrigerator, the amount and the temperature of the (meth)acrylic acid-containing solution or the (meth)acrylic acid crystal. The flow rate of the cooling medium or the heating medium discharged from the refrigerator is preferably maintained constant. When the flow rate of the cooling medium or the heating medium discharged from the refrigerator is maintained constant, crystallizing or melting operation is easily conducted stably in the crystallizer in cooperation with the temperature thereof being maintained constant.

In the producing process of the present invention, the refrigerator used in the crystallizing step may be the same as or different from the refrigerator used in the melting step; however, in view of efficiently producing (meth)acrylic acid, the refrigerator used in the crystallizing step is preferably the same as the refrigerator used in the melting step.

Any crystallizer can be used in the producing process of the present invention as long as the crystallizer is capable of crystallizing (meth)acrylic acid. In the crystallizing step, the cooling medium is supplied to the crystallizer from the refrigerator, and as a result, (meth)acrylic acid is crystallized from the (meth)acrylic acid-containing solution. In the melting step, the heating medium is supplied to the crystallizer from the refrigerator, and as a result, the (meth)acrylic acid crystal is melted.

Preferably, the crystallizer used in the producing process of the present invention is provided with a heat-transfer surface, and (meth)acrylic acid is crystallized by heat exchange via the heat-transfer surface. In this case, it is preferred that the interior of the crystallizer is partitioned by the heat-transfer surface into a part where the cooling medium or the heating medium is supplied to (i.e. a medium-present part) and a part where the (meth)acrylic acid-containing solution and/or the (meth)acrylic acid crystal is present (i.e. a crystal-present part).

In the case where the crystallizer is provided with the heat-transfer surface, (meth)acrylic acid is crystallized by heat exchange with the (meth)acrylic acid-containing solution on the heat-transfer surface in the crystallizing step and the crystallized (meth)acrylic acid is melt in the melting step. In detail, in the crystallizing step, the (meth)acrylic acid-containing solution is supplied to the crystallizer while the cooling medium is supplied to the crystallizer, whereby the (meth)acrylic acid-containing solution is cooled by the cooling medium via the heat-transfer surface and (meth)acrylic acid is crystallized. In the melting step, the heating medium is supplied to the crystallizer, whereby the crystallized (meth)acrylic acid itself is heated by the heating medium via the heat-transfer surface to melt. Or the (meth)acrylic acid crystal may be melted by (meth)acrylic acid solution heated by the heating medium.

As the crystallizer having the heat-transfer surface, an apparatus used as a heat exchanger generally can be employed, and particularly, an apparatus used as a heat exchanger in which heat is exchanged between liquids is preferably employed. For example, a plate-type heat exchanger comprising a single plate or a plurality of plates stacked at intervals, wherein the medium-present part(s) and the crystal-present part(s) are alternately disposed while being separated by the plate(s); a multitubular (shell-and-tube) heat exchanger comprising a plurality of tubes in a vessel, wherein heat is exchanged between the interiors and exteriors of the tubes; a double-pipe heat exchanger comprising an outer pipe and an inner pipe disposed in the outer pipe, wherein heat is exchanged between the interior and exterior of the inner pipe; a coil heat exchanger comprising one coil-shaped tube disposed in a vessel, wherein heat is exchanged between the interior and exterior of the tube; a spiral plate exchanger comprising a center tube whose cross-section is divided into two parts and two heat exchanger plates winding the center tube in whorl, whereby two whorl-like paths are formed; or the like may be employed. A cross-sectional shape of the tubes used in the multitubular heat exchanger, the double-pipe heat exchanger, the coil heat exchanger and the spiral plate exchanger is not particularly limited.

In the crystallizing step, the cooling medium which has been supplied to the crystallizer receives heat by heat exchange with the (meth)acrylic acid-containing solution, whereby the cooling medium is heated. Generally, at the beginning of the crystallizing step, the cooling medium receives a large amount of heat, and at the end of the crystallizing step, the cooling medium receives a small amount of heat. For example, provided that temperature and a flow rate of the cooling medium supplied to the crystallizer is constant, the temperature of the cooling medium discharged from the crystallizer is high at the beginning of the crystallizing step and drops as the progress of crystallizing. The temperature of the cooling medium discharged from the crystallizer varies, for example, more than about 10° C. between the beginning and the end of the crystallizing step, though it depends on conditions. Therefore, when the cooling medium discharged from the crystallizer is directly fed to the refrigerator, the temperature of the cooling medium fed to the refrigerator changes greatly and the cooling load of the refrigerator changes. As a result, the operation of the refrigerator is destabilized and the consumption energy of the refrigerator is increased.

In the melting step, the heating medium which has been supplied to the crystallizer releases heat by heat exchange with the (meth)acrylic acid crystal, whereby the heating medium is cooled. Generally, at the beginning of the heating step, the heating medium releases a large amount of heat, and at the end of the melting step, the heating medium releases a small amount of heat. For example, provided that temperature and a flow rate of the heating medium supplied to the crystallizer is constant in the melting step, the temperature of the heating medium discharged from the crystallizer is low at the beginning of the melting step and rises as the progress of melting. The temperature of the heating medium discharged from the crystallizer possibly varies, for example, more than about 10° C. between the beginning and the end of the melting step, though it depends on conditions. Therefore, when the heating medium discharged from the crystallizer is directly fed to the refrigerator, the temperature of the heating medium fed to the refrigerator changes greatly and the heating load of the refrigerator changes. As a result, the operation of the refrigerator is destabilized and the consumption energy of the refrigerator is increased.

Therefore, in the process for producing (meth)acrylic acid of the present invention, a first and/or second adjustment operation, and/or, a third and/or fourth adjustment operation, which are described below, are employed for the purpose of reducing the range of the temperature change of the cooling medium or/and the heating medium returned to the refrigerator, irrespective of the temperature change of the cooling medium or the heating medium discharged from the crystallizer.

In the crystallizing step, temperature of the cooling medium to be returned to the refrigerator is maintained constant at temperature $T2$ by the first adjustment operation and/or the second adjustment operation, using a first buffer tank. In the melting step, temperature of the heating medium to be returned to the refrigerator is maintained constant at temperature $T4$ by the third adjustment operation and/or the fourth adjustment operation, using a second buffer tank.

In the present invention, a buffer tank in which the cooling medium is stored is referred to as a first buffer tank, and a buffer tank in which the heating medium is stored is referred to as a second buffer tank. The first buffer tank and the second buffer tank are referred to collectively as a buffer tank.

The buffer tank is provided with two openings, namely, an upper opening and a lower opening. No limitation is placed on the buffer tank as long as the cooling medium or the heating medium can be stored in the buffer tank, and any particular structures may not be installed in the buffer tank.

The buffer tank retains a certain amount of the cooling medium or the heating medium having a temperature gradient in a vertical direction such that an upper part is high-temperature and a lower part is low-temperature. The amount of the cooling medium or the heating medium retained in the buffer tank is appropriately determined by the temperature and the amount of the cooling medium or the heating medium discharged from the refrigerator, the performance of the refrigerator, the temperature and the amount of the (meth)acrylic acid-containing solution supplied to the crystallizer, the temperature of the cooling medium or the heating medium retained in the buffer tank, and the like.

In order that the cooling medium or the heating medium is retained in the buffer tank so as to form the temperature gradient in the vertical direction such that the upper part is high-temperature and the lower part is low-temperature, it is only necessary to feed the cooling or heating medium having high temperature into the buffer tank through the upper opening and feed the cooling or heating medium having low temperature into the buffer tank through the lower opening, whereby the temperature gradient in the vertical direction is naturally formed in the cooling medium or the heating medium retained in the buffer tank.

The shape of the buffer tank is not particularly limited, and practical cylindrical shape such as circular cylinder and multangular cylinder is preferable. Distance between the upper opening and the lower opening of the buffer tank is preferably equal to or more than a maximum cross-section length of the buffer tank, more preferably more than twice the maximum cross-section length, and further more preferably more than four times the maximum cross-section length. Thus, the distance between the upper opening and the lower opening of the buffer tank is at least equal to a width of the buffer tank, and when the buffer tank has such a shape, the temperature gradient in the vertical direction is easily formed in the cooling medium or the heating medium retained in the buffer tank.

Concerning the maximum cross-section length of the buffer tank, for example, in the case where the shape of the buffer tank is a circular cylinder, the maximum cross-section length of the buffer tank corresponds to the diameter of the circular bottom, and in the case where the shape of the buffer tank has a rectangular cylinder, the maximum cross-section length of the buffer tank corresponds to the length between the opposing corners of the rectangular bottom. In the case where the shape of the buffer tank is a cylinder except the lower part and the shape of the lower part is a pyramid or a cone narrowing downward, the maximum cross-section length of the buffer tank corresponds to the maximum cross-section length of the part having a cylindrical shape. In the case where the buffer tank has such a shape that the intermediate part in the vertical direction thereof widen, the maximum cross-section length of the buffer tank corresponds to the maximum cross-section length at the widest part of the intermediate part.

The upper opening and the lower opening are arranged in the buffer tank so that the upper opening is located above the lower opening. When the respective openings are arranged in this manner, the cooling medium or the heating medium is retained in the buffer tank so that a fluid level thereof is positioned at the upper opening.

As the upper opening and the lower opening, for example, openings may be formed on the outer surface of the buffer tank, or pipes opening into the interior of the buffer tank may be installed to the buffer tank. Preferably, as the upper opening, a pipe which opens upward in the interior of the buffer tank is installed to the buffer tank. As the lower opening, an opening is preferably formed at the bottom of the buffer tank. Both the upper opening and the lower opening are provided preferably such that the openings are located at the center of the cross-section of the buffer tank. By providing the upper opening and the lower opening in this manner, the temperature gradient of the cooling or heating medium retained in the buffer tank is easily maintained when the cooling or heating medium is inflowed or outflowed through the respective openings.

An example of connecting a buffer tank to a refrigerator and a crystallizer is explained referring to FIG. 1. In FIG. 1, a first buffer tank 41 and a second buffer tank 51 connect to a refrigerator 1 and a crystallizer 11. Here, in the present invention, both of the first buffer tank 41 and the second buffer tank 51 do not need to connect to the refrigerator 1 and the crystallizer 11, and it is only necessary that at least one of the first buffer tank 41 and the second buffer tank 51 connects to the refrigerator 1 and the crystallizer 11.

The refrigerator 1 is provided with a cooling medium-supply port 2 which supplies a cooling medium, a cooling medium-return port 3 which the cooling medium is returned to, a heating medium-supply port 6 which supplies a heating medium, a heating medium-return port 7 which the heating medium is returned to. The crystallizer 11 has a medium-present part 12 where the medium is supplied and a (meth) acrylic acid-present part 13 where a (meth)acrylic acid-containing solution and/or a (meth)acrylic acid crystal is present. The medium-present part 12 is provided with a inlet 14 and an outlet 15, and the (meth)acrylic acid-present part 13 is provided with a inlet 16 and an outlet 17.

The cooling medium discharged from the refrigerator 1 is supplied to the crystallizer 11 and heat-exchanged with a (meth)acrylic acid-containing solution in the crystallizer 11, thereby obtaining a (meth)acrylic acid crystal. Then, the cooling medium is discharged from the crystallizer 11 and returned to the refrigerator 1. Meanwhile, the heating medium discharged from the refrigerator 1 is supplied to the crystallizer 11 and heat-exchanged with the (meth)acrylic acid crystal in the crystallizer 11, thereby obtaining a (meth) acrylic acid melt. Then, the heating medium is discharged from the crystallizer 11 and returned to the refrigerator 1.

The first buffer tank 41 is provided with an upper opening 42 connected to the outlet 15 of the medium-present part 12 of the crystallizer 11 and the cooling medium-return port 3 of the refrigerator 1. Further, the first buffer tank 41 is provided with a lower opening 43 connected to the cooling medium-supply port 2 of the refrigerator 1 and/or the outlet 15 of the medium-present part 12 of the crystallizer 11, and the cooling medium-return port 3 of the refrigerator 1.

The second buffer tank 51 is provided with an upper opening 52 connected to the heating medium-supply port 6 of the refrigerator 1 and/or the outlet 15 of the medium-present part 12 of the crystallizer 11, and the heating medium-return port 7 of the refrigerator 1. Further, the second buffer tank 51 is provided with a lower opening 53 connected to the outlet 15 of the medium-present part 12 of the crystallizer 11 and the heating medium-return port 7 of the refrigerator 1.

Figure 2:
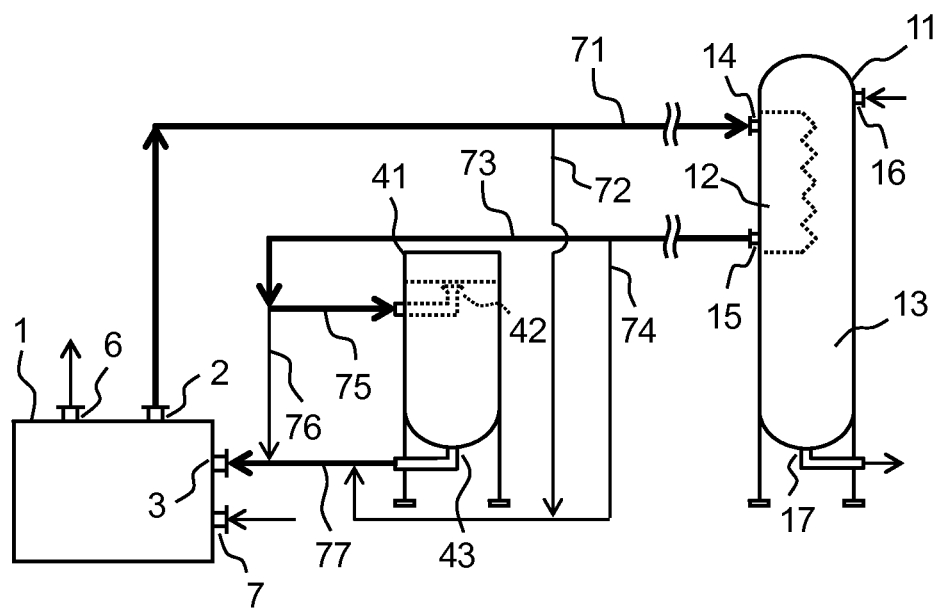
FIG. 2 shows a method for using the first buffer tank in the case where the cooling medium to be returned to the refrigerator has high temperature.
Figure 3:
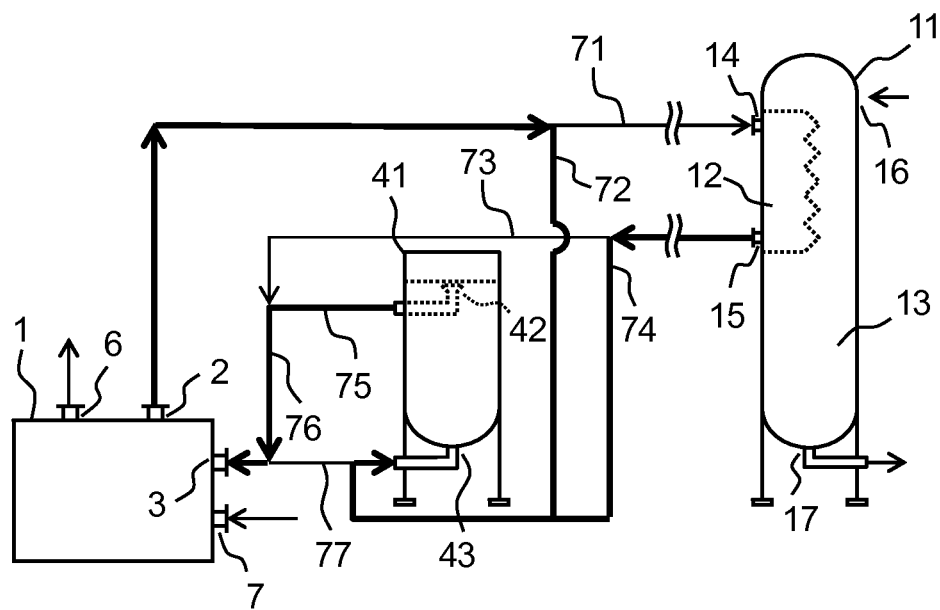
FIG. 3 shows a method for using the first buffer tank in the case where the cooling medium to be returned to the refrigerator has low temperature.

A method for using the first buffer tank in the crystallizing step, the first adjustment operation, and the second adjustment operation are explained referring to FIGS. 2 and 3.

The first adjustment operation is explained referring to FIG. 2. The first adjustment operation is conducted when the temperature of the cooling medium to be returned to the refrigerator is high in the crystallizing step.

For example, the temperature of the cooling medium discharged from the crystallizer 11 tends to be high at the beginning of the crystallizing step, and therefore, when this cooling medium discharged from the crystallizer 11 is directly retuned to the refrigerator 1, the high-temperature cooling medium comes to be returned to the refrigerator 1. In this case, a flow through a path 76 is decreased by a valve or the like, and at least a part of the cooling medium to be returned to the refrigerator 1 from the crystallizer 11 is fed into an upper part of a first buffer tank 41 through a path 75. Since the first buffer tank 41 retains a certain amount of the cooling medium having a temperature gradient such that the upper part is high-temperature and the lower part is low-temperature, when the high-temperature cooling medium is fed to the first buffer tank 41 through the upper opening 42, the high-temperature cooling medium comes to be stored at the upper part of the first buffer tank 41 so as to keep the temperature gradient of the cooling medium in the first buffer tank 41. On the other hand, the low-temperature cooling medium is discharged from the lower opening 43 of the first buffer tank 41. On this occasion, it is preferred that the amount of the cooling medium in the first buffer tank 41 is maintained constant, and therefore, the amount of the cooling medium discharged from the lower part of the first buffer tank 41 is preferably equal to the amount of the cooling medium fed to the upper part of the first buffer tank 41. The low-temperature cooling medium discharged from the lower part of the first buffer tank 41 is returned to the refrigerator 1 solely or along with the cooling medium discharged from the crystallizer 11 and carried through the path 76. Further, the low-temperature cooling medium discharged from the lower part of the first buffer tank 41 may be incorporated with a part of the cooling medium discharged from the refrigerator 1 and carried thorough a path 72. Therefore, the cooling medium whose temperature has been adjusted to be lower than that of the cooling medium discharged from the crystallizer 11 is returned to the refrigerator 1.

The second adjustment operation is explained referring to FIG. 3. The second adjustment operation is conducted when the temperature of the cooling medium to be returned to the refrigerator is low in the crystallizing step.

For example, at the end of the crystallizing step, the temperature of the cooling medium discharged from the crystallizer 11 tends to be low, and therefore, when this cooling medium discharged from the crystallizer 11 is directly retuned to the refrigerator 1, the low-temperature cooling medium comes to be returned to the refrigerator 1. In this case, a flow through a path 71 is decreased by a valve or the like, and at least a part of its flow is made to run through a path 72, whereby at least a part of the cooling medium to be supplied to the crystallizer 11 from the refrigerator 1 is fed into the lower part of the first buffer tank 41. Or a flow through a path 73 is decreased and at least a part of its flow is made to run through a path 74, whereby at least a part of the cooling medium to be returned to the refrigerator 1 from the crystallizer 11 is fed into the lower part of the first buffer tank 41. Since the first buffer tank 41 retains a certain amount of the cooling medium having the temperature gradient such that the upper part is high-temperature and the lower part is low-temperature, when the low-temperature cooling medium is fed to the first buffer tank 41 through the lower opening 43, the low-temperature cooling medium comes to be stored at the lower part of the first buffer tank 41 so as to keep the temperature gradient of the cooling medium in the first buffer tank 41. On the other hand, the high-temperature cooling medium is discharged from the upper opening 42 of the first buffer tank 41. On this occasion, it is preferred that the amount of the cooling medium in the first buffer tank 41 is maintained constant, and therefore, the amount of the cooling medium discharged from the upper part of the first buffer tank 41 is preferably equal to the amount of the cooling medium fed to the lower part of the first buffer tank 41. The high-temperature cooling medium discharged from the upper part of the first buffer tank 41 is returned to the refrigerator 1 solely or along with the cooling medium discharged from the crystallizer 11 and carried through the path 73. Therefore, the cooling medium whose temperature has been adjusted to be higher than that of the cooling medium discharged from the crystallizer 11 is returned to the refrigerator 1. The high-temperature cooling medium discharged from the upper part of the first buffer tank 41 may be incorporated with a part of the cooling medium discharged from the refrigerator 1 and carried thorough paths 72, 77.

According to the second adjustment operation, the cooling medium fed to the lower part of the first buffer tank 41 is at least a part of the cooling medium to be supplied to the crystallizer 11 from the refrigerator 1 and/or at least a part of the cooling medium to be returned to the refrigerator 1 from the crystallizer 11; and preferably, at least a part of the cooling medium to be supplied to the crystallizer 11 from the refrigerator 1 is fed to the lower part of the first buffer tank 41. In this case, since the cooling medium to be supplied to the crystallizer 11 from the refrigerator 1 has lower temperature than the cooling medium to be returned to the refrigerator 1 from the crystallizer 11, the amount of cold energy per unit volume of the cooling medium stored at the lower part of the first buffer tank 41 is more increased, and therefore, it becomes possible to store the low-temperature cooling medium efficiently. In addition, the temperature of the cooling medium to be returned to the refrigerator 1 from the crystallizer 11 varies depending on the progress of crystallizing; however, on the other hand, the temperature of the cooling medium to be supplied to the crystallizer 11 from the refrigerator 1 is almost constant, and hence, it becomes easy to control the temperature of cooling medium stored at the lower part of the first buffer tank 41.

In the crystallizing step, the first buffer tank 41 may be in a state of not being used when the cooling medium to be returned to the refrigerator 1 has the temperature T2 without utilizing the first buffer tank 41. That is, in the crystallizing step, there may be a state that the cooling medium discharged from the crystallizer 11 is directly returned to the refrigerator 1 without flowing through the first buffer tank 41.

As explained above, in the crystallizing step, the temperature of the cooling medium to be returned to the refrigerator 1 can be maintained constant at the temperature T2 by the first adjustment operation and/or the second adjustment operation, irrespective of a load change in the crystallizing step. As a result, in the crystallizing step, heat load of the refrigerator is easily maintained constant, the refrigerator works stably, and the consumption energy of the refrigerator is decreased.

Figure 4:
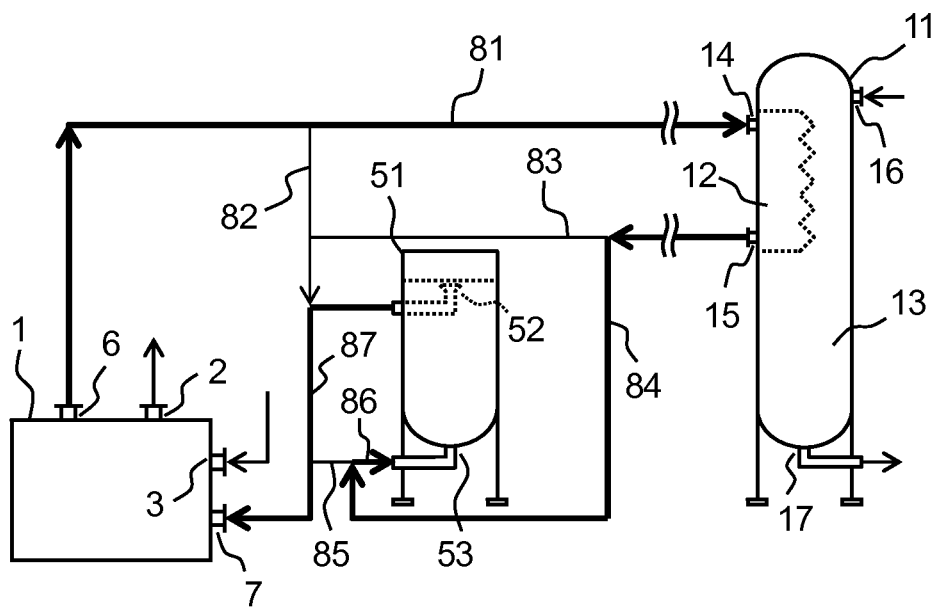
FIG. 4 shows a method for using the second buffer tank in the case where the heating medium to be returned to the refrigerator has low temperature.
Figure 5:
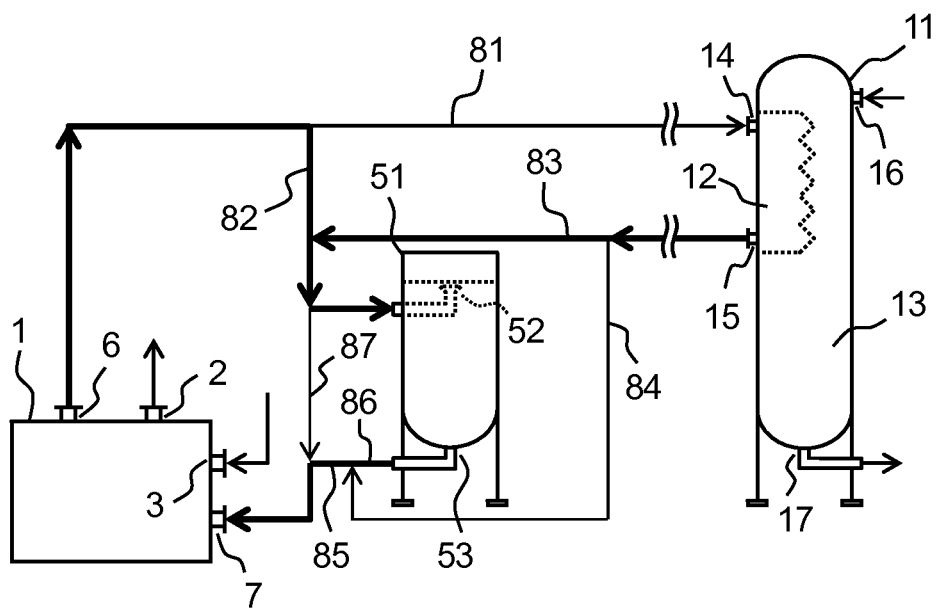
FIG. 5 shows a method for using the second buffer tank in the case where the heating medium to be returned to the refrigerator has high temperature.

A method for using the second buffer tank in the melting step, the third adjustment operation, and the fourth adjustment operation are explained referring to FIGS. 4 and 5.

The third adjustment operation is explained referring to FIG. 4. The third adjustment operation is conducted when the temperature of the heating medium to be returned to the refrigerator is low in the melting step.

For example, the temperature of the heating medium discharged from the crystallizer 11 tends to be low at the beginning of the melting step, and therefore, when this heating medium discharged from the crystallizer 11 is directly retuned to the refrigerator 1, the low-temperature heating medium comes to be returned to the refrigerator 1. In this case, a flow through a path 85 is decreased by a valve or the like, and at least a part of the heating medium to be returned to the refrigerator 1 from the crystallizer 11 is fed into a lower part of a second buffer tank 51 through a path 86. Since the second buffer tank 51 retains a certain amount of the heating medium having a temperature gradient such that the upper part is high-temperature and the lower part is low-temperature, when the low-temperature heating medium is fed to the second buffer tank 51 through the lower opening 53, the low-temperature heating medium comes to be stored at the lower part of the second buffer tank 51 so as to keep the temperature gradient of the heating medium in the second buffer tank 51. On the other hand, the high-temperature heating medium is discharged from the upper opening 52 of the second buffer tank 51. On this occasion, it is preferred that the amount of the heating medium in the second buffer tank 51 is maintained constant, and therefore, the amount of the heating medium discharged from the upper part of the second buffer tank 51 is preferably equal to the amount of the heating medium fed to the lower part of the second buffer tank 51. The high-temperature heating medium discharged from the upper part of the second buffer tank 51 is returned to the refrigerator 1 solely or along with the heating medium discharged from the crystallizer 11 and carried through the path 85. Further, the high-temperature heating medium discharged from the upper part of the second buffer tank 51 may be incorporated with a part of the heating medium discharged from the refrigerator 1 and carried thorough a path 82. Therefore, the heating medium whose temperature has been adjusted to be higher than that of the heating medium discharged from the crystallizer 11 is returned to the refrigerator 1.

The fourth adjustment operation is explained referring to FIG. 5. The fourth adjustment operation is conducted when the temperature of the heating medium to be returned to the refrigerator is high in the melting step.

For example, at the end of the melting step, the temperature of the heating medium discharged from the crystallizer 11 tends to be high, and therefore, when this heating medium discharged from the crystallizer 11 is directly retuned to the refrigerator 1, the high-temperature heating medium comes to be returned to the refrigerator 1. In this case, a flow through a path 81 is decreased by a valve or the like, and at least a part of its flow is made to run through a path 82, whereby at least a part of the heating medium to be supplied to the crystallizer 11 from the refrigerator 1 is fed into the upper part of the second buffer tank 51. Or a flow through a path 84 is decreased and at least a part of its flow is made to run through a path 83, whereby at least a part of the heating medium to be returned to the refrigerator 1 from the crystallizer 11 is fed into the upper part of the second buffer tank 51. Since the second buffer tank 51 retains a certain amount of the heating medium having the temperature gradient such that the upper part is high-temperature and the lower part is low-temperature, when the high-temperature heating medium is fed to the second buffer tank 51 through the upper opening 52, the high-temperature heating medium comes to be stored at the upper part of the second buffer tank 51 so as to keep the temperature gradient of the heating medium in the second buffer tank 51. On the other hand, the low-temperature heating medium is discharged from the lower opening 53 of the second buffer tank 51. On this occasion, it is preferred that the amount of the heating medium in the second buffer tank 51 is maintained constant, and therefore, the amount of the heating medium discharged from the lower part of the second buffer tank 51 is preferably equal to the amount of the heating medium fed to the upper part of the second buffer tank 51. The low-temperature heating medium discharged from the lower part of the second buffer tank 51 is returned to the refrigerator 1 solely or along with the heating medium discharged from the crystallizer 11 and carried through the path 84. Therefore, the heating medium whose temperature has been adjusted to be lower than that of the heating medium discharged from the crystallizer 11 is returned to the refrigerator 1. The low-temperature heating medium discharged from the lower part of the second buffer tank 51 may be incorporated with a part of the heating medium discharged from the refrigerator 1 and carried thorough paths 82, 87.

According to the fourth adjustment operation, the heating medium fed to the upper part of the second buffer tank 51 is at least a part of the heating medium to be supplied to the crystallizer 11 from the refrigerator 1 and/or at least a part of the heating medium to be returned to the refrigerator 1 from the crystallizer 11; and preferably, at least a part of the heating medium to be supplied to the crystallizer 11 from the refrigerator 1 is fed to the upper part of the second buffer tank 51. In this case, since the heating medium to be supplied to the crystallizer 11 from the refrigerator 1 has higher temperature than the heating medium to be returned to the refrigerator 1 from the crystallizer 11, the amount of heating energy per unit volume of the heating medium stored at the upper part of the second buffer tank 51 is more increased, and therefore, it becomes possible to store the high-temperature heating medium efficiently. In addition, the temperature of the heating medium to be returned to the refrigerator 1 from the crystallizer 11 varies depending on the progress of melting; however, on the other hand, the temperature of the heating medium to be supplied to the crystallizer 11 from the refrigerator 1 is almost constant, and hence, it becomes easy to control the temperature of heating medium stored at the upper part of the buffer tank 4.

In the melting step, the second buffer tank 51 may be in a state of not being used when the heating medium to be returned to the refrigerator 1 has the temperature T4 without utilizing the second buffer tank 51. That is, in the melting step, there may be a state that the heating medium discharged from the crystallizer 11 is directly returned to the refrigerator 1 without flowing through the second buffer tank 51.

As explained above, in the melting step, the temperature of the heating medium to be returned to the refrigerator can be maintained constant at the temperature T4 by the third adjustment operation and/or the fourth adjustment operation, irrespective of a load change in the melting step. As a result, in the melting step, heat load of the refrigerator is easily maintained constant, the refrigerator works stably, and the consumption energy of the refrigerator is decreased.

Hereinafter, it is explained that the crystallizing step and the melting step are respectively performed at least once, thereby producing the purified (meth)acrylic acid from the crude (meth)acrylic acid solution in the process for producing (meth)acrylic acid of the present invention.

In FIG. 1, the crude (meth)acrylic acid solution to be supplied to the crystallizer is once stored in a crude (meth)acrylic acid tank 10. On the occasion of a start of crystallizing in the crystallizer 11, the crude (meth)acrylic acid solution is transferred to a circulation tank 18 from the crude (meth)acrylic acid tank 10.

In the crystallizing step, the crude (meth)acrylic acid solution is supplied to the crystallizer 11 from the circulation tank 18 and cooled by the cooling medium, thereby obtaining a (meth)acrylic acid crystal. The crude (meth)acrylic acid solution which has not been crystallized may be returned to the circulation tank 18 and supplied to the crystallizer 11 again, whereby the crude (meth)acrylic acid solution may be circulated between the circulation tank 18 and the crystallizer 11. The remained crude (meth)acrylic acid solution which has not crystallized in the end in the crystallizing step is discharged as impurities through a path 19.

In the melting step, the (meth)acrylic acid crystal formed in the crystallizer 11 is heated by the heating medium, thereby obtaining a (meth)acrylic acid melt. In the case where the sweating operation, by which the (meth)acrylic acid crystal is partially melted and impurities present between the crystals or on the surface of the crystal are washed away, is conducted in early phase of the melting step, a melt generated by the sweating operation is discharged as impurities through the path 19.

In the case where the crystallizing step and the melting step are conducted only once, respectively, the (meth)acrylic acid melt obtained in the above is discharged through the path 19 to recover as the purified (meth)acrylic acid.

In the case where the crystallizing step and the melting step are conducted twice or more times, respectively, the (meth)acrylic acid melt obtained in the above is transferred to the circulation tank 18 and again subjected to the crystallizing step. Also, in this case, the (meth)acrylic acid melt may be circulated between the circulation tank 18 and the crystallizer 11. The remained (meth)acrylic acid melt which has not been crystallized in the end in the crystallizing step is discharged as impurities through the path 19. The (meth)acrylic acid melt obtained by conducting the crystallizing step and the melting step twice or more times in rotation is discharged through the path 19 to recover as the purified (meth)acrylic acid.

In the process for producing (meth)acrylic acid of the present invention, it is preferred that the crystallizing step and the melting step are respectively performed at least once using two or more of the crystallizer, thereby obtaining the purified (meth)acrylic acid from the crude (meth)acrylic acid solution. The number of the crystallizer is preferably the same as the number of kinds of the mediums discharged from the refrigerator, and the kinds of the mediums supplied to the respective crystallizer are preferably different from each other. As a result, the cooling medium and the heating medium discharged from the refrigerator are utilized effectively both in the crystallizing step and the melting step.

For example, in FIG. 1, two kinds of the mediums, the cooling medium and the heating medium, are discharged from the refrigerator 1, however, when the crystallizing step is conducted in the crystallizer 11, the heating medium discharged from the refrigerator is not utilized, and when the melting step is conducted in the crystallizer 11, the cooling medium discharged from the refrigerator is not utilized. Thus, potential heats of the cooling medium and the heating medium are not utilized effectively.

Figure 6:
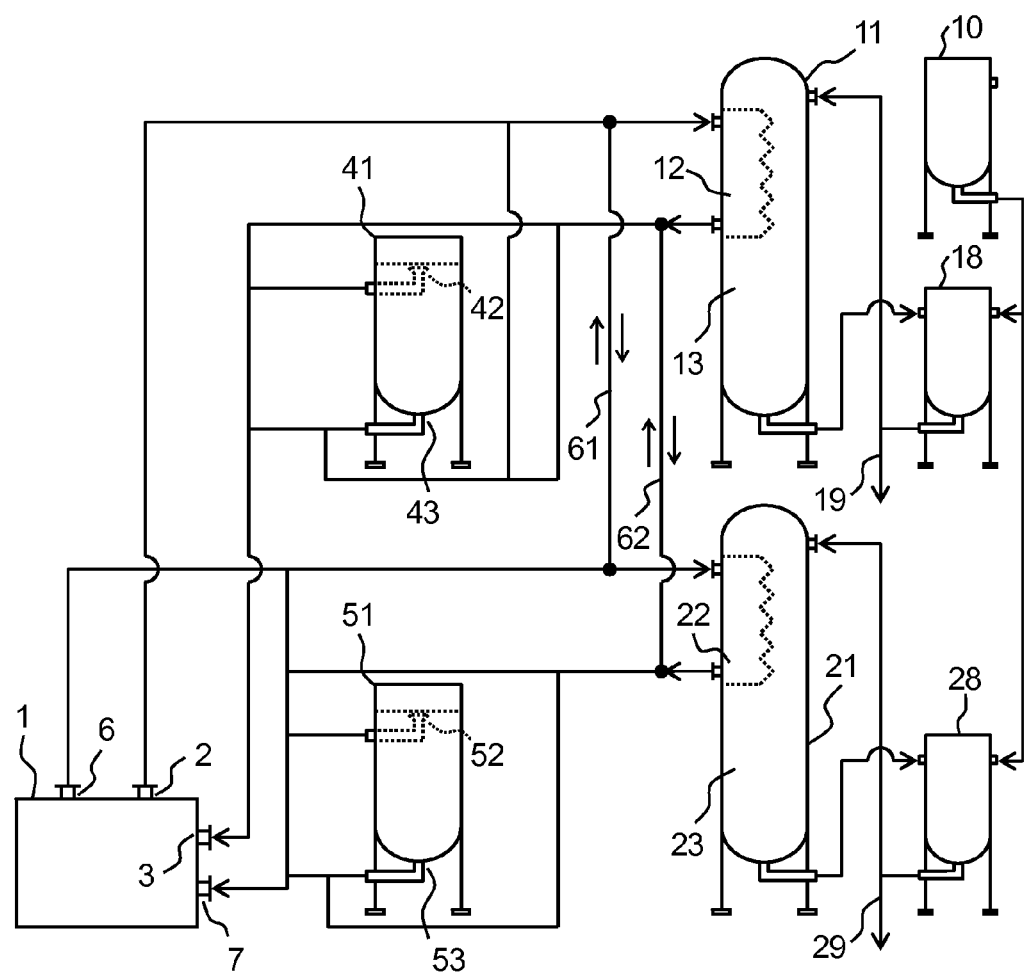
FIG. 6 shows one refrigerator, two crystallizers, two buffer tanks and flow paths connecting them.

Meanwhile, FIG. 6 shows the embodiment in which two crystallizers are provided in the embodiment shown in FIG. 1. In FIG. 6, two crystallizers, that is, a first crystallizer 11 and a second crystallizer 21, are provided as the crystallizer. The first crystallizer 11 has a first medium-present part 12 and a first (meth)acrylic acid-present part 13, and a circulation path is formed between the first crystallizer 11 and a first circulation tank 18. The second crystallizer 21 has a second medium-present part 22 and a second (meth)acrylic acid-present part 23, and a circulation path is formed between the second crystallizer 21 and a second circulation tank 28. A path 29 functions the same way as the path 19. A crude (meth)acrylic acid solution is transferred from a crude (meth)acrylic acid tank 10 to the first circulation tank 18 and the second circulation tank 28 at intervals.

The cooling medium and the heating medium discharged from the refrigerator 1 are respectively supplied to the second crystallizer 21 and the first crystallizer 11 via a path 61, and the cooling medium discharged from the second crystallizer 21 and the heating medium discharged from the first crystallizer 11 are returned to the refrigerator 1 via a path 62. Each of the paths 61 and 62 has a path for the cooling medium and a path for the heating medium.

In the embodiment shown in FIG. 6, when the crystallizing step is conducted by supplying the cooling medium to the first crystallizer, the heating medium is supplied to the second crystallizer, thereby conducting the melting step in the second crystallizer. In addition, when the crystallizing step is conducted in the second crystallizer, the melting step is conducted in the first crystallizer. Therefore, (meth)acrylic acid is efficiently produced, and both the cooling medium and the heating medium discharged from the refrigerator is effectively utilized.

Figure 7:
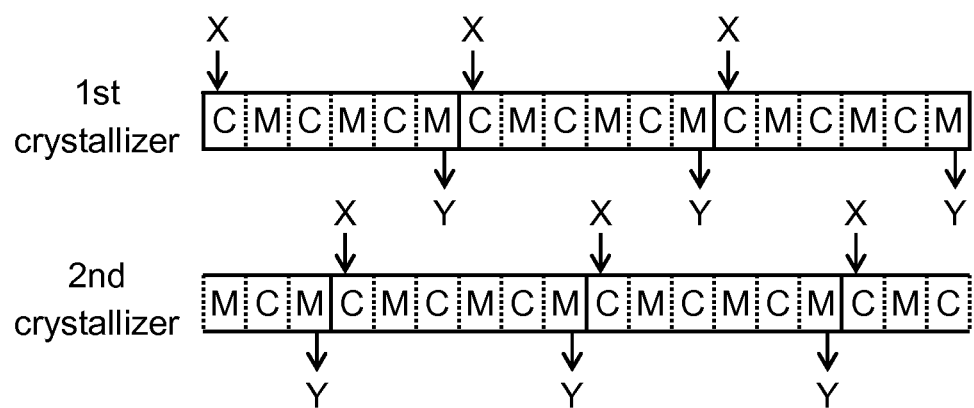
FIG. 7 shows a method for operating respective crystallizers in the embodiment shown in FIG. 6.

An example of an operation pattern of the crystallizing step and the melting step in rotation in the first crystallizer and the second crystallizer, by which the purified (meth)acrylic acid is obtained from the crude (meth)acrylic acid solution, is shown in FIG. 7. In FIG. 7, a horizontal axis represents a time passage, and time goes on from the left to the right. The crystallizing step is represented by a letter "C", the melting step is represented by a letter "M", a moment of supplying the crude (meth)acrylic acid solution is represented by a letter "X", and a moment of discharging the purified (meth)acrylic acid from the crystallizer is represented by a letter "Y".

In the each crystallizer, the crystallizing step and the melting step are respectively performed three times in rotation, thereby obtaining the purified (meth)acrylic acid from the crude (meth)acrylic acid solution. To the (meth)acrylic acid-containing solution to be subjected to second or more rounds of the crystallizing step, the crude (meth)acrylic acid solution, a (meth)acrylic acid solution obtained by one or more times of crystallization, or a (meth)acrylic acid melt discharged as impurities in another melting step is preferably added, thereby adjusting loads in the each crystallizing step and the each melting step.

At the same point in time, the mediums different from each other are supplied to the respective crystallizers, and the steps different from each other are performed in the respective crystallizers. Therefore, the respective crystallizing steps and the respective melting steps are preferably performed during the same time in order to make qualities of the purified (meth)acrylic acid obtained in the first and second crystallizes uniform as much as possible.

In the process for producing (meth)acrylic acid of the present invention, the temperature $T2$ and/or $T4$ is adjusted depending on a production amount of the purified (meth)acrylic acid per unit time, that is explained below.

The production amount of the purified (meth)acrylic acid per unit time means a mass amount of the obtained purified (meth)acrylic acid divided by time for obtaining the purified (meth)acrylic acid from the crude (meth)acrylic acid solution (hereinafter may be referred to as a "period for producing the purified (meth)acrylic acid"), in producing the purified (meth)acrylic acid from the crude (meth)acrylic acid. In FIG. 7, the production amount of the purified (meth)acrylic acid per unit time is a mass amount of the purified (meth)acrylic acid discharged at the Y divided by time for repeatedly performing the crystallizing step and the melting step three times in rotation. Here, the above explanation concerns the case where crystallization is conducted in a batch process; and in the case where crystallization is performed in a continuous process, the production amount of the purified (meth)acrylic acid per unit time means, for example, a production amount of the (meth)acrylic acid per an hour.

As a method for changing the production amount of the purified (meth)acrylic acid per unit time, it is thought of a method where the period for producing the purified (meth)acrylic acid is lengthened by pausing the operation of the refrigerator after the (meth)acrylic acid crystal is obtained in the crystallizing step, for example. However, in the operation of the refrigerator, it is not preferable to repeat of operating the refrigerator on and off frequently.

As a method for changing the production amount of the purified (meth)acrylic acid per unit time, it is also thought of a method where the period for producing the purified (meth)acrylic acid is lengthened by providing time for making the cooling medium to pass through the crystallizer in an unloaded condition (that is a condition where the cooling medium does not receive heat in the crystallizer, in the case of the cooling medium) after the (meth)acrylic acid crystal is obtained in the crystallizing step, for example. In this case, when the time for making the cooling medium to pass through the crystallizer in the unloaded condition is short, the temperature of the cooling medium to be returned to the refrigerator could be adjusted by the second adjustment operation; however, when the time is extended, the high-temperature cooling medium retained in the first buffer tank is depleted and the low-temperature cooling medium comes to be returned to the refrigerator. As a result, the operation of the refrigerator is extremely destabilized, that possibly causes a sudden shutdown of the refrigerator.

Therefore, in the producing process of the present invention, in order to change the production amount of the purified (meth)acrylic acid per unit time, the temperature $T2$ of the cooling medium returned to the refrigerator and/or the temperature $T4$ of the heating medium returned to the refrigerator is altered.

The case of decreasing the production amount of the purified (meth)acrylic acid per unit time in the crystallizing step, that is the case where the production amount of the (meth)acrylic acid crystal per unit time is decreased to below a norm, is assumed. In this case, it is thought of a method where time for the crystallizing step is lengthened relative to in a normal condition or a method where the amount of the (meth)acrylic acid-containing solution subjected to the crystallizing step is decreased relative to in a normal condition. When the time for the crystallizing step is lengthened relative to in the normal condition, the time for making the cooling medium to pass through the crystallizer in the unloaded condition is increased by the lengthened time duration. When the amount of the (meth)acrylic acid-containing solution subjected to the crystallizing step is decreased relative to in the normal condition, the crystallizing step ends earlier than in the normal condition, resulting in increasing the time for making the cooling medium to pass through the crystallizer in the unloaded condition. Thus, in the each case, the time for making the cooling medium to pass through the crystallizer in the unloaded condition is increased relative to in the normal condition.

In the case where the cooling medium is made to pass through the crystallizer in the unloaded condition, the temperature of the cooling medium to be returned to the refrigerator needs to be adjusted by the second adjustment operation. However, if the temperature $T2$ of the cooling medium returned to the refrigerator is not altered from that in the normal condition, increase of the time for making the cooling medium to pass through the crystallizer in the unloaded condition causes heavy usage of the second adjustment operation, resulting in increasing the amount of the low-temperature cooling medium and decreasing the amount of the high-temperature cooling medium, retained in the first buffer tank, relative to in the normal condition. In this case, the high-temperature cooling medium in the first buffer tank is depleted in due course.

Therefore, in the producing process of the present invention, when the production amount of the (meth)acrylic acid crystal per unit time is decreased relative to in the normal condition in the crystallizing step, the temperature $T2$ of the cooling medium returned to the refrigerator is set to be lower. When the temperature $T2$ of the cooling medium returned to the refrigerator is set to be lower, a consumed amount of the high-temperature cooling medium in the first buffer tank is decreased, and as a result, the amounts of the low-temperature cooling medium and the high-temperature cooling medium in the first buffer tank can be maintained at the same level as in the normal condition.

In the case where the producing amount of the (meth)acrylic acid crystal per unit time is increased relative to in the normal condition in the crystallizing step, the time for making the cooling medium to pass through the crystallizer in the unloaded condition is decreased relative to in the normal condition, contrary to the above. Thus, the second adjustment operation is less utilized relative to in the normal condition, resulting in decreasing the amount of the low-temperature cooling medium and increasing the amount of the high-temperature cooling medium, retained in the first buffer tank, relative to in the normal condition.

Therefore, when the production amount of the (meth) acrylic acid crystal per unit time is increased relative to in the normal condition in the crystallizing step, the temperature T2 of the cooling medium returned to the refrigerator is adjusted to be higher. When the temperature T2 of the cooling medium returned to the refrigerator is adjusted to be higher, the consumed amount of the high-temperature cooling medium in the first buffer tank is increased, and as a result, the amounts of the low-temperature cooling medium and the high-temperature cooling medium in the first buffer tank can be maintained at the same level as in the normal condition.

As explained above, in the crystallizing step, the temperature T2 is adjusted to be lower as the production amount of the purified (meth)acrylic acid per unit time is decreased, and the temperature T2 is adjusted to be higher as the production amount of the purified (meth)acrylic acid per unit time is increased, whereby the amounts of the low-temperature cooling medium and the high-temperature cooling medium retained in the first buffer tank can be maintained at the same level as in the normal condition, and hence, it becomes possible to utilize the first buffer tank for a longer period. As a result, the refrigerator can be stably operated for a longer period.

The case of decreasing the production amount of the purified (meth)acrylic acid per unit time in the melting step, that is the case where the production amount of the (meth)acrylic acid melt per unit time is decreased to below a norm, is assumed. In this case, time for making the heating medium to pass through the crystallizer in the unloaded condition (that is a condition where the heating medium does not release heat in the crystallizer, in the case of the heating medium) is increased, similarly to the case in the crystallizing step. In the case where the heating medium is made to pass through the crystallizer in the unloaded condition, the temperature of the heating medium to be returned to the refrigerator needs to be adjusted by the fourth adjustment operation. However, if the temperature T4 of the heating medium returned to the refrigerator is not altered from that in the normal condition, increase of the time for making the heating medium to pass through the crystallizer in the unloaded condition causes heavy usage of the fourth adjustment operation, resulting in increasing the amount of the high-temperature heating medium and decreasing the amount of the low-temperature heating medium, retained in the second buffer tank, relative to in the normal condition. In this case, the low-temperature heating medium in the second buffer tank is depleted in due course.

Therefore, in the producing process of the present invention, when the production amount of the (meth)acrylic acid melt per unit time is decreased relative to in the normal condition in the melting step, the temperature T4 of the heating medium returned to the refrigerator is set to be higher. When the temperature T4 of the heating medium returned to the refrigerator is set to be higher, a consumed amount of the low-temperature heating medium in the second buffer tank is decreased, and as a result, the amounts of the low-temperature heating medium and the high-temperature heating medium in the second buffer tank can be maintained at the same level as in the normal condition.

In the case where the producing amount of the (meth) acrylic acid melt per unit time is increased relative to in the normal condition in the melting step, the time for making the heating medium to pass through the crystallizer in the unloaded condition is decreased relative to in the normal condition, contrary to the above. Thus, the fourth adjustment operation is less utilized relative to in the normal condition, resulting in decreasing the amount of the high-temperature heating medium and increasing the amount of the low-temperature heating medium, retained in the second buffer tank, relative to in the normal condition.

Therefore, when the production amount of the (meth) acrylic acid melt per unit time is increased relative to in the normal condition in the melting step, the temperature T4 of the heating medium returned to the refrigerator is adjusted to be lower. When the temperature T4 of the heating medium returned to the refrigerator is adjusted to be lower, the consumed amount of the low-temperature heating medium in the second buffer tank is increased, and as a result, the amounts of the low-temperature heating medium and the high-temperature heating medium in the second buffer tank can be maintained at the same level as in the normal condition.

As explained above, the temperature T4 is adjusted to be higher as the production amount of the purified (meth)acrylic acid per unit time is decreased, and the temperature T4 is adjusted to be lower as the production amount of the purified (meth)acrylic acid per unit time is increased, whereby the amounts of the low-temperature heating medium and the high-temperature heating medium retained in the second buffer tank can be maintained at the same level as in the normal condition, and hence, it becomes possible to utilize the second buffer tank for a longer period. As a result, the refrigerator can be stably operated for a longer period.

In adjusting the temperature T2 depending on the production amount of the purified (meth)acrylic acid per unit time, it is only necessary that a mean value of the temperature T2 during the crystallizing step from supplying the crude (meth) acrylic acid solution into the crystallizer to obtaining the purified (meth)acrylic acid is adjusted as desired. When the mean temperature T2 is adjusted, the amounts of the low-temperature cooling medium and the high-temperature cooling medium retained in the first buffer tank can be maintained suitably at the time when the purified (meth)acrylic acid is obtained finally, irrespective of variation of the temperature T2 in some degree in the crystallizing step. Similarly, it is only necessary that a mean value of the temperature T4 during the melting step from supplying the crude (meth)acrylic acid solution into the crystallizer to obtaining the purified (meth) acrylic acid is adjusted as desired.

In the producing process of the present invention, in order to change the production amount of the purified (meth)acrylic acid per unit time, it is preferred that length of time for the each step is changed while the amount of the (meth)acryli acid-containing solution subjected to the crystallizing step is kept the same level as in the normal condition. When the amount of (meth)acrylic acid subjected to the crystallizing step is kept constant, crystallizing can be performed without changing operation conditions, thereby stabilizing obtaining the purified (meth)acrylic acid. Therefore, in the present invention, it is more preferable that the temperatures T2 and T4 are adjusted depending on the period for producing the purified (meth)acrylic acid while the production amount of the purified (meth)acrylic acid is kept constant. Thus, in the crystallizing step, it is preferable that the temperature T2 is adjusted while the production amount of the (meth)acrylic acid crystal is kept constant, and in the melting step, it is preferable that the temperature T4 is adjusted while the production amount of the (meth)acrylic acid melt is kept constant.

In the producing process of the present invention, the temperatures T2 and/or T4 may be adjusted depending on a supplied amount of the crude (meth)acrylic acid solution per unit time. The supplied amount of the crude (meth)acrylic acid solution per unit time is a mass amount of the crude (meth)acrylic acid solution supplied to the crystallizer divided by time for obtaining the purified (meth)acrylic acid from the crude (meth)acrylic acid solution in producing the purified (meth)acrylic acid from the crude (meth)acrylic acid. In FIG. 7, the supplied amount of the crude (meth)acrylic acid solution per unit time is a mass amount of the crude (meth) acrylic acid solution supplied at the X divided by time for repeatedly performing the crystallizing step and the melting step three times in rotation. Further, in this case, it is preferable that length of time for obtaining the purified (meth) acrylic acid from the crude (meth)acrylic acid is changed while the supplied amount of the crude (meth)acrylic acid solution is kept constant.

In adjusting the temperatures T2 and T4 depending on the production amount of the purified (meth)acrylic acid per unit time, its adjusting range is preferably within 5° C., more preferably within 4° C., and even more preferably within 3° C. When the adjusting range of the temperatures T2 and T4 is within 5° C., cooling or heating load of the refrigerator falls within suitable range and the refrigerator can stably work.

In the process for producing (meth)acrylic acid in the present invention, the cooling medium may include a first cooling medium and a second cooling medium whose temperature is lower than the temperature of the first cooling medium. For example, a refrigerator supplying the first cooling medium, the second cooling medium and a heating medium is used, and (meth)acrylic acid may be produced by combining three crystallizers and three buffer tanks with this refrigerator. In this case, the (meth)acrylic acid-containing solution is cooled by the first cooling medium, thereby conducting a first crystallizing step, that is a former part of the crystallizing step, and a cooled (meth)acrylic acid-containing solution is crystallized by the second cooling medium, thereby conducting a second crystallizing step, that is a latter part of the crystallizing step. When the first cooling medium and the second cooling medium are provided like this, saving of energy in the crystallizing step can be achieved. In the first crystallizing step, a part of (meth)acrylic acid may be crystallized when a crude (meth)acrylic acid is cooled by the first cooling medium. This embodiment is explained referring to FIG. 8.

Figure 8:
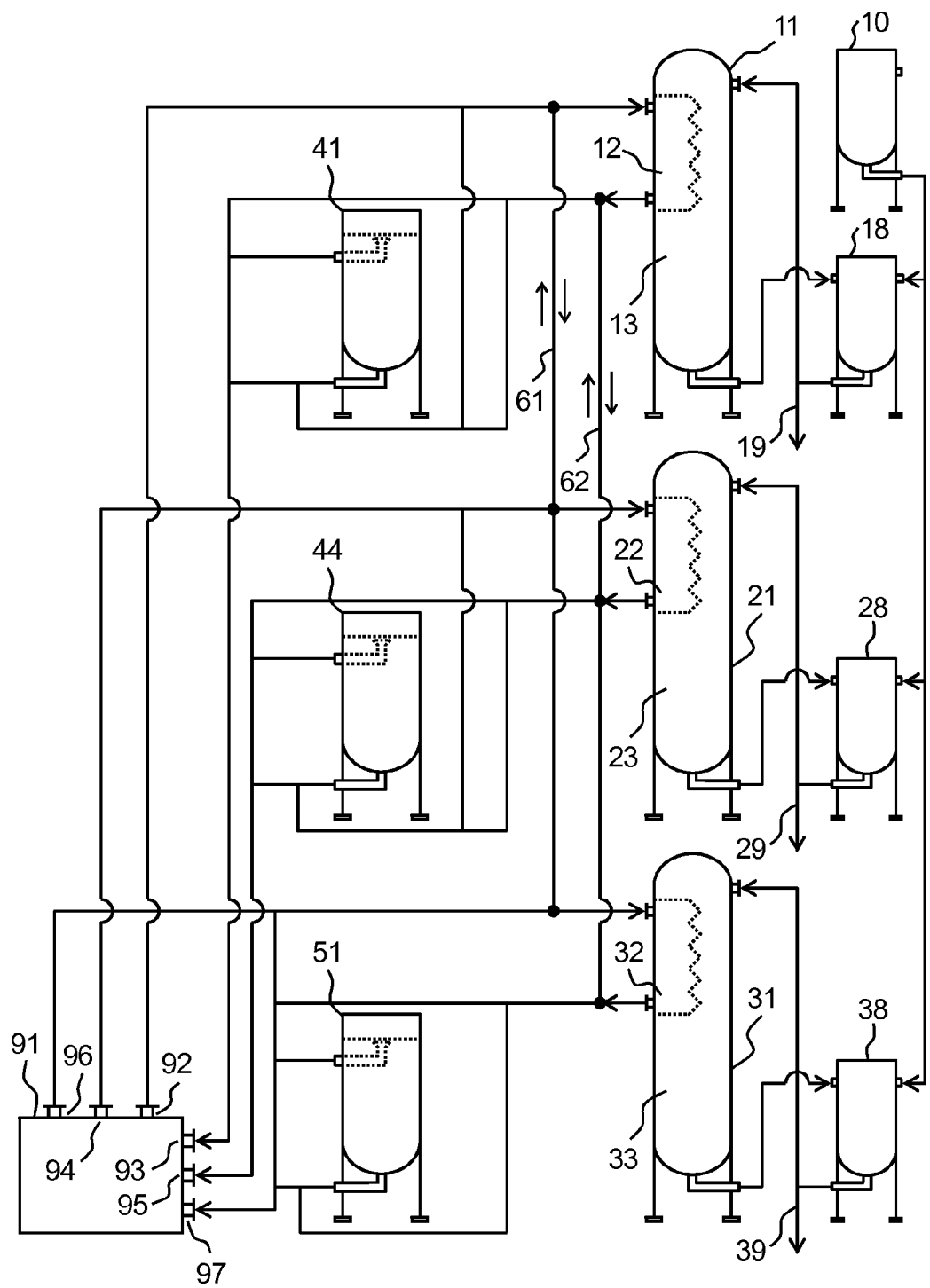
FIG. 8 shows one refrigerator, three crystallizers, three buffer tanks and flow paths connecting them.

In FIG. 8, a first cooling medium is supplied from a refrigerator 91 through a first cooling medium-supply port 92 and returned to the refrigerator 91 through a first cooling medium-return port 93, a second cooling medium is supplied from the refrigerator 91 through a second cooling medium-supply port 94 and returned to the refrigerator 91 through a second cooling medium-return port 95, and a heating medium is supplied from the refrigerator 91 through a heating medium-supply port 96 and returned to the refrigerator 91 through a heating medium-return port 97. Temperature of the first cooling medium discharged from the refrigerator is maintained constant at temperature T11, temperature of the second cooling medium discharged from the refrigerator is maintained constant at temperature T13, and temperature of the heating medium discharged from the refrigerator is maintained constant at temperature T15.

As the crystallizer, three crystallizers of a first crystallizer 11, a second crystallizer 21 and a third crystallizer 31 are provided. The first crystallizer 11 and the second crystallizer 21 are explained above. The third crystallizer 31 has a third medium-present part 32 and a third (meth)acrylic acid-present part 33, and a circulation path is formed between the third crystallizer 31 and a third circulation tank 38. A path 39 functions the same way as the path 19. A crude (meth)acrylic acid solution is transferred from the crude (meth)acrylic acid tank 10 to the first circulation tank 18, the second circulation tank 28 and the third circulation tank 38 at intervals.

The first cooling medium, the second cooling medium and the heating medium discharged from the refrigerator 91 are respectively supplied to the crystallizers 11, 21, 31 via a path 61 and returned to the refrigerator 91 via a path 62. Each of the paths 61 and 62 has a path for the first cooling medium, a path for the second cooling medium and a path for the heating medium.

Temperature of the first cooling medium returned to the refrigerator 91 is maintained constant at temperature T12 by the first adjustment operation and/or the second adjustment operation using a first buffer tank (1) 41. Temperature of the second cooling medium returned to the refrigerator 91 is maintained constant at temperature T14 by the first adjustment operation and/or the second adjustment operation using a first buffer tank (2) 44. Temperature of the heating medium returned to the refrigerator 91 is maintained constant at temperature T16 by the third adjustment operation and/or the fourth adjustment operation using a second buffer tank 51.

In the embodiment shown in FIG. 8, for example, when the first crystallizing step is conducted by supplying the first cooling medium to the first crystallizer, the second cooling medium is supplied to the second crystallizer, thereby conducting the second crystallizing step, and the heating medium is supplied to the third crystallizer, thereby conducting the melting step. In this case, the process for producing (meth) acrylic acid of the present invention comprises: a first crystallizing step of supplying a first cooling medium from a refrigerator 91 to a first crystallizer 11 and returning the first cooling medium from the first crystallizer 11 to the refrigerator 91, thereby cooling a (meth)acrylic acid-containing solution; a second crystallizing step of supplying a second cooling medium from the refrigerator 91 to a second crystallizer 21 and returning the second cooling medium from the second crystallizer 21 to the refrigerator 91, thereby obtaining a (meth)acrylic acid crystal from the cooled (meth)acrylic acid-containing solution; and a melting step of supplying a heating medium from the refrigerator 91 to the third crystallizer 31 and returning the heating medium from the third crystallizer 31 to the refrigerator 91, thereby melting the (meth)acrylic acid crystal.

Figure 9:
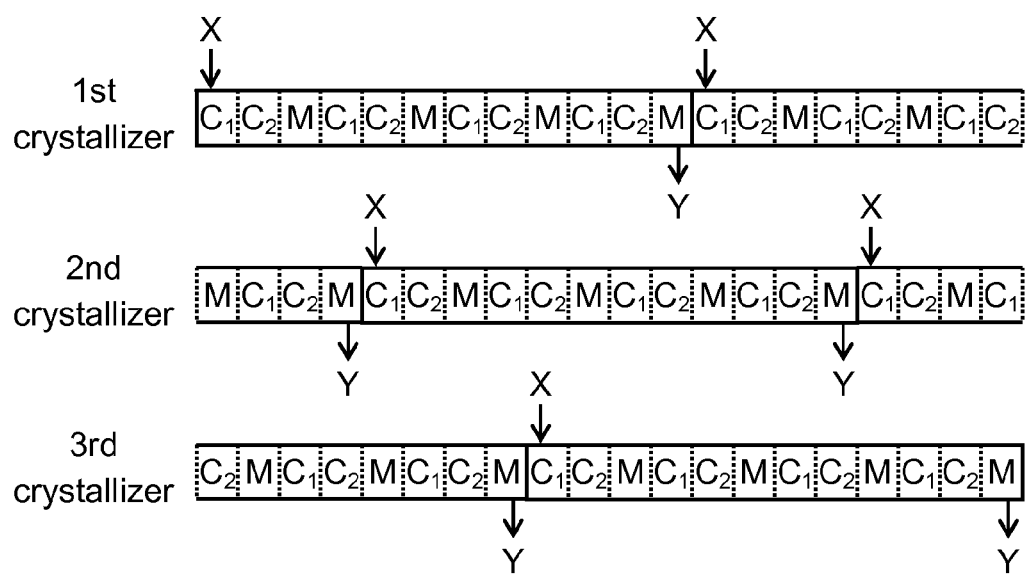
FIG. 9 shows a method for operating respective crystallizers in the embodiment shown in FIG. 8.

FIG. 9 shows an example of an operation pattern of the steps with time conducted in the respective crystallizers in the embodiment shown in FIG. 8. In FIG. 9, a horizontal axis represents a time passage, and time goes on from the left to the right. The first crystallizing step is represented by a letter "$C_1$", the second crystallizing step is represented by a letter "$C_2$", the melting step is represented by a letter "M", the moment of supplying the crude (meth)acrylic acid solution is represented by a letter "X", and the moment of discharging the purified (meth)acrylic acid from the crystallizer is represented by a letter "Y". In the each crystallizer, the first crystallizing step, the second crystallizing step and the melting step are respectively performed four times in rotation, thereby obtaining the purified (meth)acrylic acid from the crude (meth)acrylic acid solution. At the same point in time, the mediums different from each other are supplied to the respective crystallizers, and the steps different from each other are performed in the respective crystallizers. In FIG. 9, the crude (meth)acrylic acid solution is supplied to any one of the crystallizers at intervals.

In the embodiment shown in FIGS. 8 and 9, the temperature T22 of the first cooling medium, the temperature T24 of the second cooling medium, and/or the temperature T26 of the heating medium, which mediums are returned to the refrigerator 91, is adjusted depending on the production amount of the purified (meth)acrylic acid per unit time. In FIG. 9, the production amount of the purified (meth)acrylic acid per unit time is a mass amount of the purified (meth)acrylic acid discharged at the Y divided by time for repeatedly performing the first crystallizing step, the second crystallizing step and the melting step four times in rotation.

In the embodiment shown in FIGS. 8 and 9, when the production amount of the purified (meth)acrylic acid per unit time is decreased, the temperature T22 of the first cooling medium and/or the temperature T24 of the second cooling medium returned to the refrigerator 91 may be adjusted to be lower, and the temperature T26 of the heating medium may be adjusted to be higher. When the production amount of the purified (meth)acrylic acid per unit time is increased, the temperature T22 of the first cooling medium and/or the temperature T24 of the second cooling medium returned to the refrigerator 91 may be adjusted to be higher, and the temperature T26 of the heating medium may be adjusted to be lower.

According to the embodiment shown in FIGS. 8 and 9, (meth)acrylic acid can be produced efficiently and fineness of the obtained purified (meth)acrylic acid is easily enhanced. In addition, the respective mediums discharged from the refrigerator are utilized effectively. Further, the refrigerator can be stably operated for a longer period by adjusting the temperatures T22, T24 and T26.

The process for producing (meth)acrylic acid of the present invention preferably further comprises the step of obtaining the crude (meth)acrylic acid solution. The step of obtaining the crude (meth)acrylic acid solution preferably includes a gas-phase catalytic oxidation step of producing (meth)acrylic acid-containing gas from a (meth)acrylic acid production raw material by gas-phase catalytic oxidation and a collection step of collecting the (meth)acrylic acid-containing gas with a liquid medium. Further, for the purpose of increasing (meth)acrylic acid content in the (meth)acrylic acid solution obtained by the collection step, a purification step may be provided after the collection step.

In the gas-phase catalytic oxidation step, propane, propylene, (meth)acrolein, isobutylene, or the like is used as the (meth)acrylic acid production raw material, and the (meth)acrylic acid production raw material undergoes gas-phase catalytic oxidation by molecular oxygen to produce the (meth)acrylic acid-containing gas. The gas-phase catalytic oxidation is preferably carried out using a conventionally-known oxidation catalyst.

In the collection step, the (meth)acrylic acid-containing gas obtained by the gas-phase catalytic oxidation step is collected with a liquid medium in a collection column to give the (meth)acrylic acid solution. Examples of the liquid medium include water, (meth)acrylic acid-containing water, a high boiling point solvent (e.g. diphenyl ether, biphenyl and the like), and the like. In the present invention, the (meth)acrylic acid solution obtained by the collection step may be subjected to the crystallizing step as the crude (meth)acrylic acid solution.

Further, the purification step may be provided after the collection step, and the (meth)acrylic acid solution obtained by the collection step may be purified by distillation, diffusion or the like to give the crude (meth)acrylic acid solution to be subjected to the crystallizing step.

In the process for producing (meth)acrylic acid of the present invention, the following steps can be also employed: the steps of producing (meth)acrolein by dehydrating glycerin or 2-methylglycerin and obtaining the crude (meth)acrylic acid solution by gas-phase oxidation of the (meth)acrolein; or the steps of producing hydroxypropionic acid, which is hereinafter referred to as HP, or 2-methyl-3-hydroxypropionic acid from a biomass and the like of a renewable source and obtaining the crude (meth)acrylic acid solution by dehydrating the HP. A process for obtaining crude acrylic acid by dehydration and oxidation of glycerin and a process for producing the HP and obtaining crude acrylic acid by dehydration of the HP are described below.

In the process for producing acrolein, glycerin is dehydrated in the presence of a catalyst to produce acrolein, and examples of the catalyst include a solid catalyst having an acid property. As a solid acid catalyst having an acid property, compounds having a solid acid can be used, and examples of the solid acid catalyst include (a) a crystalline metallosilicate, (b) a metal oxide, (c) a clay mineral, (d) a substance in which a mineral acid is supported on an inorganic carrier such as α-alumina, silica, zirconium oxide, titanium oxide or the like, (e) a metal salt of phosphoric acid, sulfuric acid or the like and a substance in which the metal salt is supported on an inorganic carrier such as α-alumina, silica, zirconium oxide, titanium oxide or the like.

(a) Examples of the crystalline metallosilicate include a compound which contains one or more kind(s) of T atoms selected from the group consisting of Al, B, Fe and Ga, and has a crystalline structure such as LTA, CHA, FER, MFI, MOR, BEA or MTW. (b) Examples of the metal oxide include single metal oxides such as $Al_2O_3$, $TiO_2$, $ZrO_2$, $SnO_2$ and $V_2O_5$, and complex oxides such as $SiO_2$—$Al_2O_3$, $SiO_2$—$TiO_2$, $TiO_2$—$WO_3$ and $WO_3$—$ZrO_2$. (c) Examples of the clay mineral include bentonite, kaolin and montmorillonite. (d) Examples of the substance in which a mineral acid is supported on an inorganic carrier include a substance in which phosphoric acid, sulfuric acid or the like is supported on alumina, silica, zirconia or the like. (e) Examples of the phosphoric acid and the sulfuric acid include $MgSO_4$, $Al_2(SO_4)_3$, $K_2SO_4$, $AlPO_4$, $BPO_4$, $Zr_3(PO_4)_4$.

Specifically, a solid acid disclosed in International Publications WO 2006/087083 and WO 2006/087084, that is zirconium oxide supporting phosphoric acid, sulfuric acid or tungsten oxide, may be used.

Among them, a highly stable solid catalyst is preferable, since it can be put in oxidation or reduction atmosphere of high temperature during the dehydration or a regeneration treatment. Specifically, crystalline metallosilicates, metal oxides, clay minerals and the like are preferred; and HZSM-5, which contains Al as the T atom and has a MFI structure, is preferred as the crystalline metallosilicate, and a crystalline phosphate compound is preferred and aluminum phosphate is particularly preferred as the metal oxide.

Concerning acid strength of HZSM-5, it is known that HZSM-5 has a strong acidity having peaks about −9 and −16 in Hammett acid strength parameter $H_0$ (refer to the document: Kenji Hashimoto et al., Shokubai, vol. 29, No. 6, pp. 406-409, 1987), and it is known that acid strength of aluminum phosphate changes depending on a preparing method thereof and a crystalline structure, and aluminum phosphate has weak solid acidity of +1.5 to +4.8 in Hammett acid strength parameter $H_0$ (refer to the document: Kiyoko Sakamoto et al., Nippon Kagaku Kaishi, 1995(9), pp. 681-688).

In the process for producing acrolein, acrolein is produced by a gas-phase dehydration reaction that is conducted by bringing a reaction gas containing glycerin into contact with a catalyst in any reactor selected from, for example, a fixed-bed reactor, a fluidized-bed reactor, a moving-bed reactor, and the like. However, not only the gas-phase dehydration reaction that is conducted by bringing the reaction gas containing glycerin into contact with a catalyst, but also liquid-phase dehydration reaction that is conducted by bringing a glycerin solution into contact with a catalyst can be employed. In the latter case, the liquid-phase dehydration reaction can be carried out by conventionally-known various methods such as a method of using a fixed-bed reactor and a distillation column in combination, a method of using a stirring vessel and a distillation column in combination, a method of using a single-stage stirring vessel, a method of using a multistage stirring vessel, a method of using a multistage distillation column, and combinations thereof These methods may be conducted either batch-wise or continuously, and generally conducted continuously.

A process for producing acrolein that utilizes the gas-phase dehydration reaction, which is excellent in industrial productivity of acrolein, is hereinafter explained, as an example.

The reaction gas may be a gas consisting of only glycerin or further contain an inert gas which is inactive against the dehydration reaction of glycerin so that a glycerin concentration in the reaction gas is adjusted. Examples of the inert gas include, for example, steam, nitrogen, carbon dioxide gas, and air. The glycerin concentration in the reaction gas is generally in the range of 0.1 mol % to 100 mol %, preferably 1 mol % or more, and more preferably 5 mol % or more for economically producing acrolein in high efficiency.

As the catalyst, a catalyst for dehydrating glycerin that shows high acrolein selectivity is preferably used, and using such a catalyst makes it possible to produce acrolein in high yield even when the reaction gas is introduced at a high flow rate. A flow rate of the reaction gas, a gas space velocity per unit volume of the catalyst (GHSV), is generally in the range of 50 $hr^{-1}$ to 20000 $hr^{-1}$, preferably 10000 $hr^{-1}$ or lower, and more preferably 4000 $hr^{-1}$ or lower for economically producing acrolein in high efficiency.

Reaction temperature is generally in the range of 200° C. to 500° C., preferably in the range of 250° C. to 450° C., and more preferably in the range of 300° C. to 400° C.

A pressure of the reaction gas is not particularly limited as long as it is in the range where glycerin does not become condensed, and is generally in the range of 0.001 MPa to 1 MPa, preferably in the range of 0.01 MPa to 0.5 MPa, and more preferably 0.3 MPa or lower.

When the dehydration reaction of acrolein is continuously conducted, carbonaceous matters may be deposited on the surface of the catalyst, resulting in decreasing the activity of the catalyst. Specifically, selectivity of acrolein is lowered and selectivity of propionaldehyde is enhanced. In such a case, when a regeneration treatment in which the catalyst is brought into contact with a regeneration gas at high temperature is conducted, carbonaceous matters deposited on the surface of the catalyst can be removed, thereby regenerating the activity of the catalyst. Examples of the regeneration gas include, for example, oxidative gases such as oxygen and air which contains oxygen. The regeneration gas may further contain an inert gas which is inactive against the regeneration treatment, such as nitrogen, carbon dioxide and steam, if needed. In the case where there is a risk of abrupt heat generation due to contact of the catalyst with oxygen, it is recommended that the inert gas is contained in the regeneration gas for suppressing the abrupt heat generation. Temperature required for the regeneration treatment is not particularly limited as long as the carbonaceous matters can be removed without occurring heat deterioration of the catalyst, and is preferably equal to or lower than calcination temperature in preparing the catalyst.

Crude acrolein prepared by the dehydration reaction of glycerin contains by-products. Therefore, it is preferred that the thus obtained crude acrolein is subjected to purification. Examples of the by-product include, for example, phenol, 1-hydroxyacetone, and allyl alcohol in addition to propionaldehyde. In the purification of the crude acrolein, phenol and/or 1-hydroxyacton are mainly removed. When these by-products are removed, yield of acrylic acid is enhanced in producing acrylic acid from acrolein. Especially, product amount of acetic acid can be reduced when 1-hydroxyaceton is removed.

In consideration of enhancing the yield of acrylic acid, it is considered to be preferable that a larger amount of phenol and/or 1-hydroxyacton is removed. Therefore, a mass ratio Ph/A of a mass of acrolein (A) and a mass of phenol (Ph) after the purification and a mass ratio H/A of a mass of acrolein (A) and a mass of 1-hydroxyacetone (H) after the purification are respectively preferably 0.020 or less, more preferably 0.010 or less, and further more preferably 0.005 or less. Meanwhile, when a further larger amount of phenol and/or 1-hydroxyacton is removed, loss of acrolein may be increased or the purification of acrolein may be complicated. Taking these facts into consideration, the mass ratios Ph/A and H/A are preferably $1\times10^{-9}$ or more, more preferably $1\times10^{-7}$ or more, and further more preferably $1\times10^{-5}$ or more.

Boiling points of acrolein, phenol and 1-hydroxyacetone are about 53° C., about 182° C. and about 146° C., respectively. By utilizing the differences between theses boiling points, phenol and/or 1-hydroxyacetone can be removed from the crude acrolein. Methods for that include, for example, a method of fractional-distilling acrolein having a lower boiling point than removal objectives by treating the liquid crude acrolein with a distillation column, a method of condensing removal objectives having higher boiling points than acrolein by treating the gaseous crude acrolein with a condensation column, and a method of vaporizing acrolein having a lower boiling point than removal objectives by blowing a gas into the crude acrolein introduced into a diffusion column.

In addition, melting points of acrolein, phenol and 1-hydroxyacetone are about −87° C., about 43° C. and about −17° C., respectively. By utilizing the differences between theses melting points, phenol and/or 1-hydroxyacetone can be removed from the crude acrolein. Method for that include, for example, a method of removing crystals of phenol and/or 1-hydroxyacetone by cooling the crude acrolein.

Propionaldehyde has a boiling point of about 48° C. and a melting point of about −81° C., and therefore, it is possible to remove propionaldehyde from the crude acrolein by utilizing the difference of the boiling or melting points between propionaldehyde and acrolein. However, since the both differences of the boiling point and the melting point between propionaldehyde and acrolein are small, loss of acrolein may possibly be increased. Therefore, propionaldehyde is preferably treated along with acrolein, a precursor of acrylic acid, without being separated from acrolein.

In the case of using glycerin derived from biodiesel as the raw material, the obtained crude acrolein may be used without being purified; however, it contains impurities such as phenol, 1-hydroxyacetone, methoxyacetone, 3-methoxypropanal and the like, which cause deterioration of catalyst activity, decrease of yield, or production of byproducts such as formic acid, acetic acid, propionic acid, pyruvic acid, 3-methoxypropionic acid in acrylic acid, and hence, the crude acrolein may be purified to be used. The purification can be conducted by a conventionally-known method, and examples of the purification include a method of distilling a condensed liquid of the reaction composition or a collection liquid obtained by using a collection solvent, and a method of using a purification apparatus provided with a collection column and a diffusion column, which is disclosed in Japanese Unexamined Patent Application Publication No. 2008-115103. In the case where the crude acrolein is not purified, impurities in acrylic acid may be removed by purifying acrylic acid in the subsequent step. In view of simplifying the process and lowering production cost, it is preferred that the crude acrolein is not purified to be used.

Acrylic acid can be produced by oxidizing acrolein obtained in the above process for producing acrolein. For producing acrylic acid, it is preferred that a gas containing acrolein, which may be hereinafter referred to as a "acrolein-containing gas", is brought into coexistence with a catalyst for oxidizing acrolein, which may be hereinafter referred to as a "acrolein-oxidizing catalyst", in any oxidation reactor selected from a fixed-bed reactor, a moving-bed reactor, a fluidized-bed reactor and the like at a temperature in the range of 200° C. to 400° C., thereby conducting gas-phase oxidation of acrolein. The oxidation of acrolein may be accompanied by production of propionic acid from propionaldehyde.

As the acrolein-oxidizing catalyst, any conventionally-known catalysts for oxidizing acrolein can be employed that can be used for producing acrylic acid by gas-phase catalytic oxidation of acrolein with molecular oxygen or molecular oxygen-containing gas; and examples of the acrolein-oxidizing catalyst include, for example, a mixture or a complex oxide of metal oxides such as iron oxide, molybdenum oxide, titanium oxide, vanadium oxide, tungsten oxide, antimony oxide, tin oxide, copper oxide. Among these catalysts, a molybdenum-vanadium catalyst which containing molybdenum and vanadium as essential components is particularly preferable. The acrolein-oxidizing catalyst may be a supported catalyst in which a mixture or a complex oxide of metal oxides described above is supported on a carrier (e.g. an inorganic oxide such as silica, alumina, zirconia, a complex oxide thereof, and an inorganic substance such as silicon carbide).

Concerning the feed amount of oxygen relative to the acrolein-containing gas used in the production of acrylic acid, the upper limit thereof is needed to be appropriately set, since the excess amount of oxygen may cause an explosion hazard due to combustion of acrolein.

By the gas-phase catalytic oxidation of acrolein, a gaseous substance containing crude acrylic acid is obtained. In a collection step, the gaseous substance is liquefied by cold condensation, solvent collection or the like, thereby obtaining a crude acrylic acid solution. The thus obtained crude acrylic acid can be subjected to the crystallizing step of the present invention.

A process for producing acrylic acid from a biomass or the like of a renewable source is hereinafter described. There is no direct route to produce acrylic acid from a biomass, however, acrylic acid can be produced rather easily by dehydrating hydroxycarboxylic acid such as 3-hydroxypropionic acid (hereinafter may be referred to as 3HP), which can be prepared by fermentation of sugar available from decomposition of lactic acid (hereinafter may be referred to as 2HP), cellulose or the like, which are natural substances and compassable easily. Acrylic acid can be also prepared by dehydrating a salt of hydroxycarboxylic acid.

Hydroxycarboxylic acid and/or a salt thereof is available from various resources. Biological resources which are recyclable as a carbon source are preferably used in view of global warming and protection of environment, and 2-hydroxypropionic available from natural products and 2-hydrocypropionic acid or 3-hydroxypropionic acid prepared by fermentation of sugar available from decomposition of cellulose or the like can be used.

An aqueous solution of 2-hydroxypropionic acid can be prepared by known-methods such as, for example, fermentation using lactobacillus described in the document: Advance in Applied Microbiology, vol. 42, pp. 45-95 (1996), and fermentation using fungi described in the document: Enzyme and Microbial Technology, vol. 26, pp. 87-107 (2000).

An aqueous solution of 3-hydroxypropionic acid can be also prepared by known-methods such as, for example, fermentation of glycerin as a carbon source using transgenic Escherichia coli beta-alanine aminotransferase derived from Streptomyces griseus ATCC21897 described in the document: International Publication WO 2008/027742, and fermentation of glucose as a carbon source using Escherichia coli to which glycerin dehydratase derived from Klebsiella pneumoniae and aldehyde oxidase derived from Escherichia coli are introduced described in the document: International Publication WO 2001/016346. Any bacteria or modified bacteria can be used for the fermentations, as long as the methods described in the above documents, that show examples of preparing methods of 3-hydroxypropionic acid aqueous solution, are employed; and 3-hydroxypropionic acid aqueous solution prepared by fermentation of various carbon sources using an organism capable of forming 3-hydroxypropionic acid can be used in the process of the present invention. Further, 3-hydroxypropionic acid aqueous solution prepared by contacting between sugar as a raw material and an organism without fermenting can be also converted into acrylic acid by the process of the present invention. As a manner of contacting between sugar and an organism, the embodiment of conducting reaction using a microorganism or a processed microorganism in the presence of sugar used as a raw material is included. Examples of the processed microorganism include a microorganism treated with acetone, toluene or the like, a destroyed microorganism, a lyophilized microorganism, a fractured microorganism, a cell-free extract of a fractured microorganism, and a crude enzyme liquid or a purified enzyme obtained by extracting an enzyme therefrom. Furthermore, 3-hydroxypropionic acid aqueous solution prepared by reaction using a microorganism fixed on a carrier by a common means, a processed material thereof, or an enzyme can be also used.

For producing crude acrylic acid by dehydrating hydroxycarboxylic acid, known-methods can be employed. For example, Japanese Unexamined Laid-open Patent Application Publication No. 2005-521718 discloses a method for producing unsaturated carboxylic acid or salt thereof where an aqueous solution or a solution of 2,3-hydroxycarboxylic acid (2HP and 3HP) or salt thereof prepared by fermentation is heated in the presence or the absence of a catalyst, thereby dehydrated. International Publication WO 2005/095320 discloses a method for producing 2,3-unsaturated carboxylic acid where an aqueous solution of 2,3-hydroxycarboxylic acid is fed to a place in which an inactive ceramic or an acidic or basic solid catalyst is held, and heated. International Publication WO 2007/106100 discloses a method for producing a reaction product containing 2,3-unsaturated carboxylic acid compound where a composition containing 3-hydroxycarbonyl compound is fed to a reactor in a substantive liquid form and converted in the reactor. In this method, an acid catalyst, a basic catalyst or the like is used in the reactor.

The thus obtained acrylic acid is a liquid substance or a gaseous substance containing crude acrylic acid. The liquid substance can be used as-is as the crude acrylic acid solution in the present invention. The gaseous substance is liquefied by cold condensation, solvent collection or the like in the collection step, whereby a crude acrylic acid solution can be obtained, and the crude acrylic acid solution can used in the crystallizing step of the present invention.

(Meth)acrylic acid produced by the producing process of the present invention is excellent in quality stability, and hence, when the (meth)acrylic acid is used as a monomer for producing a hydrophilic resin such as an absorbent resin and a water-soluble resin, the polymerization reaction is easily controlled and quality of the hydrophilic resin is stabilized, thereby improving various properties such as absorption performance and dispersibility of inorganic substances. Especially, since acrylic acid produced by the producing process of the present invention is excellent in quality stability and controllability in the polymerization reaction, it is quite useful as a raw material for producing an absorbent resin having high absorbency and high quality. In addition, since hydroxypropionic acid prepared by fermentation and crude acrylic acid prepared by dehydrating hydroxypropionic acid which has been prepared by fermentation contain impurities such as organic acids other than acrylic acid, it is quite effective to purify the crude acrylic acid by a crystallization operation of the present invention for obtaining acrylic acid with high-purity.

Definitions concerning the absorbent resin of the present invention and preferable embodiments for production thereof are hereinafter explained.

(1) "Absorbent Resin"

The term "absorbent resin" in the present invention means a water-swellable and water-insoluble polymer gelling agent. The term "water-swellable" means that CRC (absorption ratio under non-pressure) specified in ERT 441.2-02 is generally 5 g/g or more, and the term "water-insoluble" means Ext (water solubles) specified in ERT 470.2-02 is generally 0 mass % or more and 50 mass % or less.

The absorbent resin can be designed appropriately depending on the intended use thereof and is not particularly limited; however, it is preferably a hydrophilic cross-linked polymer prepared by cross-linking polymerization of unsaturated monomer(s) having a carboxyl group. The absorbent resin is not limited to a form where whole amount (100%) is a polymer, and may include additives and the like in a range to maintain the above properties.

In the present invention, it means an absorbent resin which is composed principally of acrylic acid and/or a salt thereof (hereinafter referred to as "acrylic acid (salt)" as a repeating unit and may contain a graft constituent as needed. Specifically, the absorbent resin contains acrylic acid (salt) generally in 50 mol % to 100 mol %, preferably in 70 mol % to 100 mol %, more preferably in 90 mol % to 100 mol %, and particularly preferably substantially in 100 mol %, among the total amount of monomer(s) used in the polymerization except a cross-linking agent.

(2) "EDANA" and "ERT"

The term "EDANA" is an abbreviation for European Disposables and Nonwovens Association, and the term "ERT" is an abbreviation for the measurement method (EDANA Recommended Test Methods) for the absorbent resin of an European standard (nearly a world standard). In the present invention, unless otherwise specified, the ERT original (known document: revised in 2002) is referred to in measuring properties of the absorbent resin.

(a) "CRC" (ERT 441.2-02)

The term "CRC" is an abbreviation for Centrifuge Retention Capacity and means an absorption ratio under non-pressure (hereinafter may be referred to as an "absorption ratio"). Specifically, it means an absorption ratio (unit: g/g) measured by having an absorbent resin swell freely in 0.9 mass % sodium chloride aqueous solution for 30 minutes and dewatering using a centrifuge.

The absorbent resin obtained in the present invention preferably has the CRC of 20 g/g or more and 100 g/g or less, more preferably 25 g/g or more and 50 g/g or less, and further more preferably 27 g/g or more and 45 g/g or less.

(b) "AAP" (ERT 442.2-02)

The term "AAP" is an abbreviation for Absorption Against Pressure and means an absorption ratio under pressure. Specifically, it means an absorption ratio (unit: g/g) measured by having an absorbent resin swell in 0.9 mass % sodium chloride aqueous solution under a pressure of 2.06 kPa for 1 hour; however, in the present invention, it means an absorption ratio (unit: g/g) measured in the condition of under a pressure of 4.83 kPa for 1 hour.

The absorbent resin obtained in the present invention preferably has the AAP of 20 g/g or more and 30 g/g or less, and more preferably 22 g/g or more and 30 g/g or less.

(c) "Ext" (ERT 470.2-02)

The term "Ext" is an abbreviation for Extractables and means water solubles (a content of water-soluble component). Specifically, it is a value (unit: mass %) of a dissolved amount of a polymer, that is measured by pH titration, when 1 g of an absorbent resin is fed to 200 g of 0.9 mass % sodium chloride aqueous solution and stirred at 500 rpm for 16 hours. The absorbent resin obtained in the present invention preferably has the Ext of 0 g/g or more and 30 g/g or less, and more preferably 0 g/g or more and 20 g/g or less.

(d) "FSC" (ERT 440.2-02)

The term "FSC" is an abbreviation for Free Swell Capacity and means a rate of freely-swelling. Specifically, it means an absorption ratio (unit: g/g) measured by having 0.20 g of an absorbent resin swell freely in 0.9 mass % sodium chloride aqueous solution for 30 minutes and not dewatering using a centrifuge.

(e) "Residual Monomers" (ERT 410.2-02)

The term "Residual Monomers (RM)" is a residual amount of monomer(s) in an absorbent resin. Specifically, it means a value (unit: ppm) is measured by a high-performance liquid chromatography, when 1.0 g of an absorbent resin is fed to 200 cm$^3$ of the 0.9 mass % sodium chloride aqueous solution and stirred at 500 rpm for 1 hour. The absorbent resin obtained in the present invention preferably has the RM of 1000 ppm or less, and more preferably 500 ppm or less.

(f) "PSD" (ERT 420.2-02)

The term "PSD" is an abbreviation for Particle Size Distribution and means a particle size distribution measured by a sieve classification. A weight average particle diameter (D50) and a particle diameter distribution width are measured by similar methods described in "(1) Average Particle Diameter and Distribution of Particle Diameter" of page 7, lines 25-43 in European Patent Publication No. 0349240.

(3) "Liquid Permeability"

The term "liquid permeability" means a liquid flow between swollen gel particles under pressure or non-pressure. As typical measurement methods of the "liquid permeability", SFC (Saline Flow Conductivity) and GBP (Gel Bed Permeability) are indicated.

"SFC (Saline Flow Conductivity)" means permeability of 0.69 mass % saline through an absorbent resin under a load of 0.3 psi. It is measured according to the SFC test method described in U.S. Pat. No. 5,669,894. The unit thereof is "cm$^3$*s*10$^{-7}$/g".

"GBP" means permeability of 0.69 mass % saline through an absorbent resin under load or freely-swelling. It is measured according to the GBP test method described in International Publication WO 2005/016393.

The absorbent resin obtained in the present invention preferably has the SFC of 1 or more, and more preferably 5 or more.

(4) Preferred Embodiments for Production

Acrylic acid and/or a salt thereof produced according to the process of the present invention is used as a main component of monomer(s), and polymerized and cross-linked using a radical polymerization initiator of about 0.001 mol % of more and 2 mol % or less and a cross-linking agent of about 0.01 mol % or more and 5 mol % or less, respectively relative to the acrylic acid and/or a salt thereof, and then dried and pulverized, thereby obtaining the absorbent resin.

Preferred producing methods in terms of higher productivity of the absorbent resin are described in, for example, U.S. Pat. Nos. 6,867,269, 6,906,159, 7,091,253 and International Publications WO 01/038402 and WO 2006/034806.

A method for polymerizing acrylic acid obtained by the process of the present invention is not particularly limited; and a continuous belt-type polymerization disclosed in U.S. Pat. Nos. 4,893,999, 6,241,928, U.S. Patent Application Publication No. 2005/215734 and the like, a continuous kneader-type polymerization and a batch kneader-type polymerization disclosed in U.S. Pat. Nos. 6,987,151, 6,710,141 and the like, are preferably employed.

The thus obtained polymer is preferably converted into a particulate absorbent resin by the producing method disclosed in U.S. Pat. Nos. 4,920,202, 5,264,495, 5,275,773, 6,207,796, 6,164,455, 6,207,796, 6,291,636, 6,875,511 or the like.

Further, the absorbent resin is preferably cross-linked on the surface thereof, depending on the purpose or application thereof, especially in the case of applying to sanitary articles. As concrete embodiments, producing methods disclosed in European Patent Publication Nos. 0349240, 0605150, 0450923, 0812873, 0450924, 0668080, Japanese Unexamined Laid-open Patent Application Publication Nos. 7-242709, 7-224304, U.S. Pat. Nos. 5,409,771, 5,597,873, 5,385,983, 5,610,220, 5,633,316, 5,674,633, 5,462,972, International Publications WO 99/42494, WO 99/43720, WO 99/42496, and the like are preferred.

The above-described publications are incorporated into the present specification by reference.

EXAMPLES

Example

Purified acrylic acid was produced from a crude acrylic acid solution using a crystallization system shown in FIG. 6. As a crystallizer, a crystallizer which is provided with a heat-transfer surface and whose interior is partitioned into a medium-present part and an acrylic acid-present part by the heat-transfer surface was used. As a refrigerator, an absorption refrigerator was employed, and temperature T1 of a cooling medium discharged from the refrigerator was maintained at −25.0° C. and temperature T3 of a heating medium discharge from the refrigerator was maintained at 40.0° C.

33.8 ton of the crude acrylic acid solution was supplied to each of the crystallizer, and the crystallizing step and the melting step were repeated three times, respectively, thereby obtaining 16.9 ton of the purified acrylic acid per crystallizer. Thus, a production amount of the purified acrylic acid per unit time was 7.5 ton/h. Operation periods of the crystallizing step and the melting step were respectively 47 minutes.

In the crystallizing step, temperature T2 of the cooling medium returned to the refrigerator was controlled at −14.9° C. by utilizing a first buffer tank. The cooling medium which has been returned to the refrigerator was cooled to −25.0° C. by the refrigerator and discharged. During this operation, performance of the refrigerator for refrigerating the cooling medium was 4800 kW. In the melting step, temperature T4 of the heating medium returned to the refrigerator was controlled at 31.0° C. by utilizing a second buffer tank. The heating medium which has been returned to the refrigerator was heated to 40.0° C. by the refrigerator and discharged. During this operation, performance of the refrigerator for refrigerating the heating medium was −4400 kW. Here, the performance of the refrigerator means "an amount of heat acquired from an object per unit time". Therefore, the performance on cooling was represented by "+" and the performance on heating was represented by "−".

Next, in order to decrease the production amount of the purified acrylic acid per unit time from 7.5 ton/h to 6.0 ton/h, respective operation periods of the crystallizing step and the melting step were extended to 59 minutes while the amounts of the crude acrylic acid solution supplied to the crystallizer for each time were maintained. During this operation, the temperature T2 of the cooling medium returned to the crystallizer was adjusted to be lowered to −16.9° C., and the temperature T4 of the heating medium returned to the crystallizer was adjusted to be raised to 32.9° C. Meanwhile, the temperature T1 of the cooling medium discharged from the refrigerator was maintained at −25.0° C., and the temperature T3 of the heating medium discharged from the refrigerator was maintained at 40.0° C. During this operation, performances of the refrigerator for refrigerating the cooling medium and the heating medium were 3800 kW and −3500 kW, respectively. Though the production amount of the purified acrylic acid per unit time was changed, the refrigerator worked stably and purified acrylic acid can be produced suitably.

Comparative Example

Purified acrylic acid was obtained at 7.5 ton/h in the same manner as the above. On this occasion, the temperature T2 of the cooling medium returned to the refrigerator was controlled at −14.9° C. by utilizing the first buffer tank in the crystallizing step and the temperature T4 of the heating medium returned to the refrigerator was controlled at 31.0° C.

Next, in order to decrease the production amount of the purified acrylic acid per unit time from 7.5 ton/h to 6.0 ton/h, respective operation periods of the crystallizing step and the melting step were extended to 59 minutes while the amounts of the crude acrylic acid solution supplied to the crystallizer for each time were maintained. However, on this occasion, the temperature T2 of the cooling medium returned to the refrigerator was maintained at −14.9° C. and the temperature T4 of the heating medium returned to the refrigerator was maintained at 31.0° C. Further, the temperature T1 of the cooling medium discharged from the refrigerator was also maintained at −25.0° C. and the temperature T3 of the heating medium discharged from the refrigerator was also maintained at 40.0° C.

Since the production amount of the purified acrylic acid per unit time was reduced, the second adjustment operation had needed to be used more frequently as to the cooling medium, resulting in decreasing the amount of high-temperature cooling medium retained in the first buffer tank. As to the heating medium, the fourth adjustment operation had needed to be used more frequently, resulting in decreasing the amount of the low-temperature heating medium retained in the second buffer tank. In due course, the high-temperature cooling medium retained in the first buffer tank and the low-temperature heating medium retained in the second buffer tank were depleted, and hence, the refrigerator worked unstably and the operation of the refrigerator was stopped.

When the operation of crystallizers was continued in this situation for a while, the amounts of the high-temperature cooling medium in the first buffer tank and the low-temperature heating medium in the second buffer tank increased, and therefore, the operation of the refrigerator was resumed. Since the production amount of the purified acrylic acid per unit time was reduced to 6.0 ton/h, it had needed to continue with the operation of the crystallizer while repeating of stopping and resuming the operation of the refrigerator. Therefore, operation cost of the refrigerator rose, resulting in increasing the production cost of the purified acrylic acid per unit time.

INDUSTRIAL APPLICABILITY

The present invention can be used for a process for producing (meth)acrylic acid comprising a crystallizing step and a melting step.

EXPLANATION OF REFERENCE 1, 91: refrigerator
2, 92, 94: cooling medium-supply port
3, 93, 95: cooling medium-return port
6, 96: heating medium-supply port
7, 97: heating medium-return port
11: first crystallizer
21: second crystallizer
31: third crystallizer
41, 44: first buffer tank
51: second buffer tank

The invention claimed is:

1. A process for producing (meth)acrylic acid, comprising:
a crystallizing step of supplying a cooling medium from a refrigerator to a crystallizer and returning the cooling medium from the crystallizer to the refrigerator, thereby obtaining a (meth)acrylic acid crystal from a (meth)acrylic acid-containing solution; and
a melting step of supplying a heating medium from a refrigerator to the crystallizer and returning the heating medium from the crystallizer to the refrigerator, thereby melting the (meth)acrylic acid crystal;
wherein:
the crystallizing step and the melting step are respectively performed at least once, thereby producing purified (meth)acrylic acid from a crude (meth)acrylic acid solution;
temperature of the cooling medium discharged from the refrigerator is maintained constant at temperature $T1$;
temperature of the cooling medium to be returned to the refrigerator is maintained constant at temperature $T2$ in the crystallizing step by a first adjustment operation and/or a second adjustment operation;
the temperature $T2$ is adjusted depending on a production amount of the purified (meth)acrylic acid per unit time;
the first adjustment operation is performed by feeding at least a part of the cooling medium to be returned to the refrigerator from the crystallizer into an upper part of a first buffer tank and discharging the cooling medium from a lower part of the first buffer tank to return to the refrigerator; and
the second adjustment operation is performed by feeding at least a part of the cooling medium to be supplied to the crystallizer from the refrigerator and/or the cooling medium to be returned to the refrigerator from the crystallizer into the lower part of the first buffer tank and discharging the cooling medium from the upper part of the first buffer tank to return to the refrigerator.

2. A process for producing (meth)acrylic acid, comprising:
a crystallizing step of supplying a cooling medium from a refrigerator to a crystallizer and returning the cooling medium from the crystallizer to the refrigerator, thereby obtaining a (meth)acrylic acid crystal from a (meth)acrylic acid-containing solution; and
a melting step of supplying a heating medium from a refrigerator to the crystallizer and returning the heating medium from the crystallizer to the refrigerator, thereby melting the (meth)acrylic acid crystal;
wherein:
the crystallizing step and the melting step are respectively performed at least once, thereby producing purified (meth)acrylic acid from a crude (meth)acrylic acid solution;
temperature of the heating medium discharged from the refrigerator is maintained constant at temperature $T3$;
temperature of the heating medium to be returned to the refrigerator is maintained constant at temperature $T4$ in the melting step by a third adjustment operation and/or a fourth adjustment operation;
the temperature $T4$ is adjusted depending on a production amount of the purified (meth)acrylic acid per unit time;
the third adjustment operation is performed by feeding at least a part of the heating medium to be returned to the refrigerator from the crystallizer into an lower part of a second buffer tank and discharging the heating medium from an upper part of the second buffer tank to return to the refrigerator; and
the fourth adjustment operation is performed by feeding at least a part of the heating medium to be supplied to the crystallizer from the refrigerator and/or the heating medium to be returned to the refrigerator from the crystallizer into the upper part of the second buffer tank and discharging the heating medium from the lower part of the second buffer tank to return to the refrigerator.

3. A process for producing (meth)acrylic acid, comprising:
a crystallizing step of supplying a cooling medium from a refrigerator to a crystallizer and returning the cooling medium from the crystallizer to the refrigerator, thereby obtaining a (meth)acrylic acid crystal from a (meth)acrylic acid-containing solution; and
a melting step of supplying a heating medium from a refrigerator to the crystallizer and returning the heating medium from the crystallizer to the refrigerator, thereby melting the (meth)acrylic acid crystal;
wherein:
the crystallizing step and the melting step are respectively performed at least once, thereby producing purified (meth)acrylic acid from a crude (meth)acrylic acid solution;
temperature of the cooling medium discharged from the refrigerator is maintained constant at temperature $T1$;
temperature of the cooling medium to be returned to the refrigerator is maintained constant at temperature $T2$ in the crystallizing step by a first adjustment operation and/or a second adjustment operation;
temperature of the heating medium discharged from the refrigerator is maintained constant at temperature $T3$;
temperature of the heating medium to be returned to the refrigerator is maintained constant at temperature $T4$ in the melting step by a third adjustment operation and/or a fourth adjustment operation;

the temperatures T2 and T4 are adjusted depending on a production amount of the purified (meth)acrylic acid per unit time;

the first adjustment operation is performed by feeding at least a part of the cooling medium to be returned to the refrigerator from the crystallizer into an upper part of a first buffer tank and discharging the cooling medium from a lower part of the first buffer tank to return to the refrigerator;

the second adjustment operation is performed by feeding at least a part of the cooling medium to be supplied to the crystallizer from the refrigerator and/or the cooling medium to be returned to the refrigerator from the crystallizer into the lower part of the first buffer tank and discharging the cooling medium from the upper part of the first buffer tank to return to the refrigerator;

the third adjustment operation is performed by feeding at least a part of the heating medium to be returned to the refrigerator from the crystallizer into an lower part of a second buffer tank and discharging the heating medium from an upper part of the second buffer tank to return to the refrigerator; and the fourth adjustment operation is performed by feeding at least a part of the heating medium to be supplied to the crystallizer from the refrigerator and/or the heating medium to be returned to the refrigerator from the crystallizer into the upper part of the second buffer tank and discharging the heating medium from the lower part of the second buffer tank to return to the refrigerator.

4. The process for producing (meth)acrylic acid according to claim 3, wherein
the temperatures T1 and T3 are fixed irrespective of the production amount of the purified (meth)acrylic acid per unit time.

5. The process for producing (meth)acrylic acid according to claim 3, wherein
the temperature T2 is adjusted to be lower and the temperature T4 is adjusted to be higher when the production amount of the purified (meth)acrylic acid per unit time is decreased.

6. The process for producing (meth)acrylic acid according to claim 3, wherein
a product amount of the purified (meth)acrylic acid obtained by performing the crystallizing step and the melting step at least once, respectively, is kept constant, and
the temperatures T2 and T4 are adjusted depending on a period for producing the purified (meth)acrylic acid.

7. The process for producing (meth)acrylic acid according to claim 3, further comprising the steps of:
dehydrating glycerin or 2-methylglycerin to convert to (meth)acrolein; and
oxidizing the (meth)acrolein to convert to (meth)acrylic acid, thereby obtaining the crude (meth)acrylic acid solution.

8. The process for producing (meth)acrylic acid according to claim 3, further comprising the step of:
dehydrating hydroxypropionic acid or 2-methyl-3-hydroxypropionic acid to convert to (meth)acrylic acid, thereby obtaining the crude (meth)acrylic acid solution.

9. A process for producing a hydrophilic resin, comprising the step of:
polymerizing a monomeric component(s) including the (meth)acrylic acid obtained by the producing process according to claim 3.

10. A process for producing an absorbent resin, comprising the step of:
polymerizing a monomeric component(s) including the (meth)acrylic acid obtained by the producing process according to claim 3.

11. The process for producing (meth)acrylic acid according to claim 1, wherein
the temperature T1 is fixed irrespective of the production amount of the purified (meth)acrylic acid per unit time.

12. The process for producing (meth)acrylic acid according to claim 1, wherein
the temperature T2 is adjusted to be lower when the production amount of the purified (meth)acrylic acid per unit time is decreased.

13. The process for producing (meth)acrylic acid according to claim 1, wherein
a product amount of the purified (meth)acrylic acid obtained by performing the crystallizing step and the melting step at least once, respectively, is kept constant, and
the temperature T2 is adjusted depending on a period for producing the purified (meth)acrylic acid.

14. The process for producing (meth)acrylic acid according to claim 2, wherein
the temperature T3 is fixed irrespective of the production amount of the purified (meth)acrylic acid per unit time.

15. The process for producing (meth)acrylic acid according to claim 2, wherein
the temperature T4 is adjusted to be higher when the production amount of the purified (meth)acrylic acid per unit time is decreased.

16. The process for producing (meth)acrylic acid according to claim 2, wherein
a product amount of the purified (meth)acrylic acid obtained by performing the crystallizing step and the melting step at least once, respectively, is kept constant, and
the temperature T4 is adjusted depending on a period for producing the purified (meth)acrylic acid.

17. The process for producing (meth)acrylic acid according to claim 1, further comprising the steps of:
dehydrating glycerin or 2-methylglycerin to convert to (meth)acrolein; and
oxidizing the (meth)acrolein to convert to (meth)acrylic acid, thereby obtaining the crude (meth)acrylic acid solution.

18. The process for producing (meth)acrylic acid according to claim 1, further comprising the step of:
dehydrating hydroxypropionic acid or 2-methyl-3-hydroxypropionic acid to convert to (meth)acrylic acid, thereby obtaining the crude (meth)acrylic acid solution.

19. A process for producing a hydrophilic resin, comprising the step of:
polymerizing a monomeric component(s) including the (meth)acrylic acid obtained by the producing process according to claim 1.

20. A process for producing an absorbent resin, comprising the step of:
polymerizing a monomeric component(s) including the (meth)acrylic acid obtained by the producing process according to claim 1.

* * * * *